United States Patent [19]

Macor

[11] Patent Number: 5,639,752

[45] Date of Patent: Jun. 17, 1997

[54] INDOLE DERIVATIVES

[75] Inventor: John Eugene Macor, Salem, Conn.

[73] Assignee: Pfizer Inc, New York, N.Y.

[21] Appl. No.: 244,043

[22] PCT Filed: Oct. 6, 1992

[86] PCT No.: PCT/US92/08306

§ 371 Date: May 20, 1994

§ 102(e) Date: May 20, 1994

[87] PCT Pub. No.: WO93/11106

PCT Pub. Date: Jun. 10, 1993

[51] Int. Cl.[6] .................. A61K 31/40; A61K 31/395; A61K 31/495; A61K 31/505

[52] U.S. Cl. .................. 514/245; 514/272; 514/323; 514/333; 514/339; 514/414; 514/266; 514/361; 514/417; 514/370; 514/375; 514/381; 544/277; 544/212; 544/333; 546/256; 546/277.4; 546/268.7; 548/466; 548/468; 548/465; 548/128; 548/455; 548/181; 548/207; 548/254

[58] Field of Search .................. 544/277, 212, 544/333; 546/273, 256; 548/466, 468, 465, 128, 455, 181, 207, 254; 514/323, 333, 339, 414, 266, 245, 361, 272, 417, 370, 375, 381

[56] References Cited

U.S. PATENT DOCUMENTS

| | | | |
|---|---|---|---|
| 4,252,803 | 2/1981 | Webb | 424/248.5 |
| 4,839,377 | 6/1989 | Bays et al. | 514/415 |
| 4,855,314 | 8/1989 | Oxford et al. | 514/415 |
| 5,245,046 | 9/1993 | Youngdale | 548/495 |
| 5,348,968 | 9/1994 | Lavielle et al. | 514/360 |
| 5,399,574 | 3/1995 | Robertson et al. | 514/339 |
| 5,409,941 | 4/1995 | Nowakowski | 514/339 |

FOREIGN PATENT DOCUMENTS

| | | |
|---|---|---|
| 0303506 | 8/1988 | European Pat. Off. . |
| 0313397 | 10/1988 | European Pat. Off. . |
| 0354777 | 8/1989 | European Pat. Off. . |

OTHER PUBLICATIONS

Mukhomorov, "Influence of electronic and steric interactions on the radioprotective properties of indolylalkylamines," Chemical Abstracts, vol. 106, No. 98661w, 1987.

Green et al., "Correlation of electronic structures of indole derivatives with their biological activities," Chemical Abstracts, vol. 74, No. 40779v, 1971.

W. Feniuk et al., P.P.A. Humphrey & M. J. Perren—Br. J. Pharmacol. (1989), 96, 83–90.

P. P. A. Humphrey et al.—Br. J. Pharmacol. (1988), 94, 1123–1132.

Elliott Shaw et al.—J. Am. Chem. Soc., 1877 (1953).

Marcel Pesson et al.—Eur. J. Med. Chem., May–Jun., (1980) 15, No. 3, pp. 269–273.

John Krapcho et al.—J. Med. Chem. 1988, 31, 1148–1160.

*Primary Examiner*—Matthew V. Grumbling
*Attorney, Agent, or Firm*—Peter C. Richardson; Paul H. Ginsburg; Grover F. Fuller, Jr.

[57] ABSTRACT

Compounds of the formula

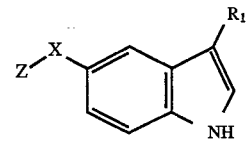

wherein Z is

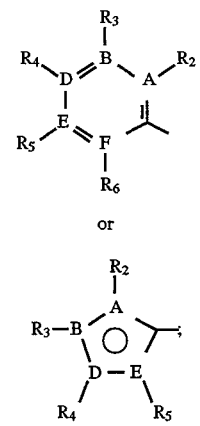

$R_1$ is

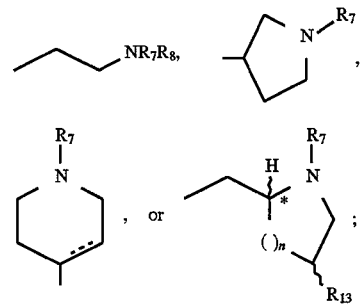

X is O, NH, or S; A, B, D, E, and F are each independently C, N, O, or S;

wherein the remaining variables are defined in the specification, and the pharmaceutically acceptable salts thereof. These compounds are useful psychotherapeutics and are potent serotonin (5-HT$_1$) agonists and may be used in the treatment of depression, anxiety, eating disorders, obesity, drug abuse, cluster headache, migraine, pain, chronic paroxysmal hemicrania and headache associated with vascular disorders, and other disorders arising from deficient serotonergic neurotransmission. The compounds can also be used as centrally acting antihypertensives and vasodilators.

16 Claims, No Drawings

INDOLE DERIVATIVES

This is the national stage under 35 U.S.C. §371 of application no. PCT/US92/08306 filed Oct. 6, 1992.

BACKGROUND OF THE INVENTION

The present invention relates to indole derivatives, to processes and intermediates for their preparation, to pharmaceutical compositions containing them and to their medicinal use. The active compounds of the present invention are useful in treating migraine and other disorders.

U.S. Pat. Nos. 4,839,377 and 4,855,314 and European Patent Application Publication Number 313397 refer to 5-substituted 3-aminoalkyl indoles. The compounds are said to be useful for the treatment of migraine.

British Patent Application 040279 refers to 3-aminoalkyl-1H-indole-5-thioamides and carboxamides. The compounds are said to be useful in treating hypertension, Raynaud's disease and migraine.

European Patent Application Publication Number 303506 refers to 3-poly:hydropyridyl-5-substituted-1H-indoles. The compound are said to have $5HT_1$-receptor agonist and vasoconstrictor activity and to be useful in treating migraine.

European Patent Application Publication Number 354777 refers to N-piperidinyl:indolyl:ethyl-alkane sulfonamide derivatives. The compound are said to have $5HT_1$-receptor agonist and vasoconstrictor activity and to be useful in treating cephalic pain.

SUMMARY OF THE INVENTION

The present invention relates to compounds of the formula

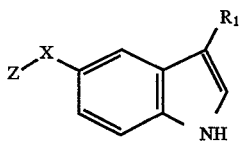

wherein Z is

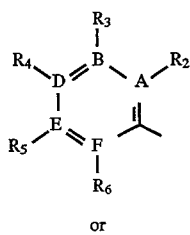

or

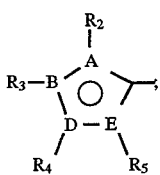

$R_1$ is equal to

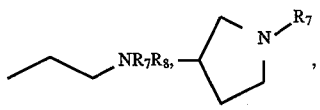

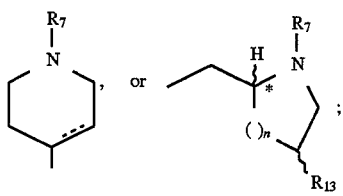

X is O, NH, or S; A, B, D, E, and F are each independently C, N, O, or S; $R_2$, $R_3$, $R_4$, $R_5$, and $R_6$ are each independently hydrogen, $C_1$ to $C_6$ alkyl, aryl, $C_1$ to $C_3$ alkyl-aryl, halogen (e.g. fluorine, chlorine, bromine or iodine), cyano, nitro, —$NR_7R_8$, —$(CH_2)_mOR_9$, —$SR_9$, —$SO_2R_9$, —$SO_2NR_7R_8$, —$NR_7SO_2R_8$, —$NR_7CO_2R_9$, —$NR_7COR_9$, —$CONR_7R_8$, or —$CO_2R_9$; one of $R_2$ and $R_3$, $R_3$ and $R_4$, $R_4$ and $R_5$, or $R_5$ and $R_6$ may be taken together to form a five- to seven-membered alkyl ring, a six-membered aryl ring, a five- to seven-membered heteroalkyl ring having 1 heteroatom of N, O, or S, or a five- to six-membered heteroaryl ring having 1 or 2 heteroatoms of N, O, or S; $R_7$ and $R_8$ are each independently hydrogen, $C_1$ to $C_6$ alkyl, —$(CH_2)_qR_{10}$, $C_1$ to $C_3$ alkyl-aryl, aryl, or $R^7$ and $R^8$ may be taken together to form a four- to six-membered ring; $R_9$ is hydrogen, $C_1$ to $C_6$ a alkyl, $C_1$ to $C_3$ alkyl-aryl, aryl, or —$(CH_2)_wR_{11}$; $R_{10}$ and $R_{11}$ are each independently —OH, —$OR_{12}$, —$CO_2R_{12}$, —$CONHR_{12}$, or cyano; $R_{12}$ is hydrogen, $C_1$ to $C_6$ alkyl, aryl, or $C_1$ to $C_6$ alkyl-aryl; $R_{13}$ is hydrogen, —$OR_{14}$, or —$NHCOR_{14}$; $R_{14}$ is to $C_1$ alkyl or $C_6$ to $C_3$ alkyl-aryl; n is 0, 1, or 2; m is 1, 2, or 3; q is 2, 3, or 4; w is 2, 3, or 4; the above aryl groups and the aryl moieties of the above alkyl-aryl groups are independently phenyl or substituted phenyl, wherein said substituted phenyl may be substituted with one to three of $C_1$ to $C_4$ alkyl, halogen, hydroxy, cyano, carboxamido, nitro, and $C_1$ to $C_4$ alkoxy; and a broken line represents an optional double bond, and the pharmaceutically acceptable salts thereof. These compounds are useful in treating migraine and other conditions discussed below.

The compounds of the invention include all optical isomers of formula I (e.g. R and S enantiomers) and their racemic and diastereomeric mixtures. When $R_1$ is equal to

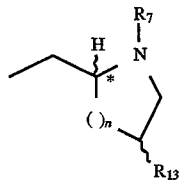

the R diastereomer with the chiral carbon designated by * are preferred. When $R_{13}$ is —$OR_{14}$ or —$NHCOR_{14}$, the cis epimers [(2R,4R) absolute configuration] are particularly preferred.

Unless otherwise indicated, the alkyl groups referred to herein, as well as the alkyl moieties of other groups referred to herein (e.g. alkoxy), may be linear or branched, and they may also be cyclic (e.g. cyclopropyl, cyclobutyl, cyclopentyl, or cyclohexyl) or be linear or branched and contain cyclic moieties.

Preferred compounds of the invention are compounds of the formula I wherein

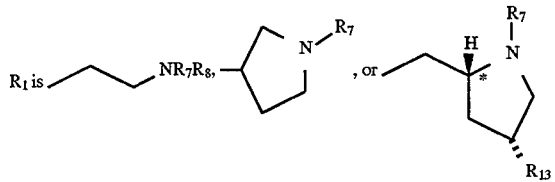

where $R_7$ and $R_8$, and $R_{13}$ are as defined above;

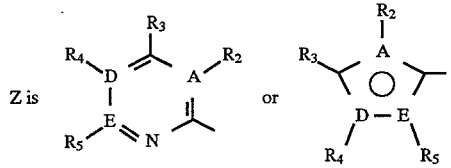

where A, D, E, $R_2$, $R_3$, $R_4$ and $R_5$ are as defined above; and X is equal to NH.

The aforementioned description of the present invention includes compounds of the following formulae

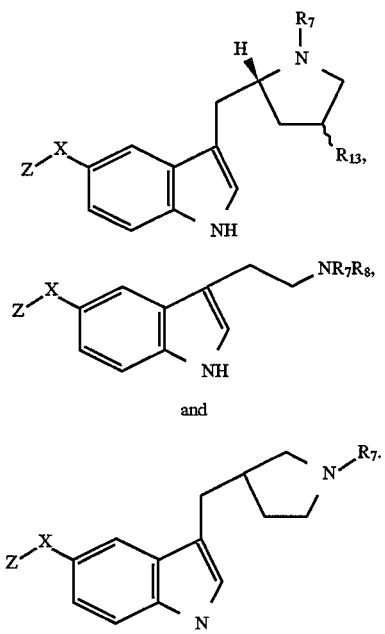

The following compounds are particularly preferred:

3-(2-dimethylaminoethyl)-5-(3,5-dinitropyrid-2-ylamino)-1H-indole;

3-(2-dimethylaminoethyl)-5-(3-nitropyrid-2-ylamino)-1H-indole;

3-(2-dimethylaminoethyl)-5-(3-trifluoromethylpyrid-2-ylamino)-1H-indole;

(R)-5-(3-nitropyrid-2-ylamino)-3-(pyrrolidin-2-ylmethyl)-1H-indole;

(R)-3-(N-methylpyrrolidin-2-ylmethyl)-5-(nitropyrid-2-ylamino)-1H-indole;

(R,S)-3-(N-methylpyrrolidin-3-yl)-5-(3-nitropyrid-2-ylamino)-1H-indole;

5-(benzoxaz-2-ylamino)-3-(2-dimethylaminoethyl)-1H-indole;

(R)-3-(N-cyclopropylmethylpyrrolidin-2-ylmethyl)-5-(3-nitropyrid-2-ylamino)-1H-indole;

(R)-5-(3-nitropyrid-2-ylamino)-3-(N-(2-propynyl)pyrrolidin-2-ylmethyl)-1H-indole;

(R)-5-(3-nitropyrid-2-ylamino)-3-(N-(2-propenyl)pyrrolidin-2-ylmethyl)-1H-indole;

(R)-5-(3-nitropyrid-2-ylamino)-3-(N-propylpyrrolidin-2-ylmethyl)-1H-indole;

(R)-3-(N-butylpyrrolidin-2-ylmethyl)-5-(3-nitropyrid-2-ylamino)-1H-indole;

(R)-3-(N-ethylpyrrolidin-2-ylmethyl)-5-(3-nitropyrid-2-ylamino)-1H-indole;

(R)-5-(3-nitropyrid-2-ylamino)-3-(N-pentylpyrrolidin-2-ylmethyl)-1H-indole;

(R)-3-(N-(2-methoxyethyl)pyrrolidin-2-ylmethyl)-5-(3-nitropyrid-2-ylamino)-1H-indole;

5-(4-benzyl-1,3-thiaz-2-ylamino)-3-(2-dimethylaminoethyl)-1H-indole;

(R)-5-(3-benzylthio-1,2,4-thiadiaz-5-ylamino)-3-(N-methylpyrrolidin-2-ylmethyl)-1H-indole;

3-(2-dimethylaminoethyl)-5-(pyrimid-2-ylamino)-1H-indole;

3-(2-dimethylaminoethyl)-5-(3-methylsulfonylpyrid-2-ylamino)-1H-indole;

(R)-3-(N-methylpyrrolidin-2-ylmethyl)-5-(2-nitrophenylamino)-1H-indole;

(R)-5-(6-methoxy-3-nitropyrid-2-ylamino)-3-(N-methylpyrrolidin-2-ylmethyl)-1H-indole;

(R)-5-(4-methyl-3-nitropyrid-2-ylamino)-3-(N-methylpyrrolidin-2-ylmethyl)-1H-indole;

(R)-3-(N-methylpyrrolidin-2-ylmethyl)-5-(3-nitro-5-phenylpyrid-2-ylamino)-1H-indole;

(R)-5-(3-cyanopyrid-2-ylamino)-3-(N-methylpyrrolidin-2-ylmethyl)-1H-indole;

(R)-5-(6-isopropoxy-3-nitropyrid-2-ylamino)-3-(N-methylpyrrolidin-2-ylmethyl)-1H-indole;

(R)-5-(4-cyano-2-nitrophenylamino)-3-(N-methylpyrrolidin-2-ylmethyl)-1H-indole;

(R)-3-(N-methylpyrrolidin-2-ylmethyl)-5-(4-trifluoromethyl-2-nitrophenylamino)-1H-indole;

(R)-5-(5,6-dichloro-2-nitrophenylamino)-3-(N-methylpyrrolidin-2-ylmethyl)-1H-indole;

5-(4-Cyano-2-nitrophenylamino)-3-[(2R,4R)-N-methyl-4-methylpyrrolidin-2-ylmethyl]-1H-indole;

(R)-5-(5-chloro-2-nitrophenylamino)-3-(N-methylpyrrolidin-2-ylmethyl)-1H-indole;

(R)-3-(N-(2-cyanoethyl)pyrrolidin-2-ylmethyl)-5-(3-nitropyrid-2-ylamino)-1H-indole; and (R)-3-(N-(2-cyanomethyl)pyrrolidin-2-ylmethyl)-5-(3-nitropyrid-2-ylamino)-1H-indole.

The following are other specific compounds of the present invention:

6-(3-(2-dimethylaminoethyl)indol-5-ylamino)purine;

3-(2-dimethylaminoethyl)-5-(2-nitrophenylamino)-1H-indole;

3-(2-dimethylaminoethyl)-5-(3-aminocarbonylpyrid-2-ylamino)-1H-indole;

3-(2-dimethylaminoethyl)-5-(2,6-dinitrophenylamino)-1H-indole;

3-(2-dimethylaminoethyl)-5-(2-cyanophenylamino)-1H-indole;

3-(2-dimethylaminoethyl)-5-(2,4-dinitrophenylamino)-1H-indole;

3-(2-dimethylaminoethyl)-5-(6-ethoxycarbonyl-3-methylthio-1,2,4-triazin-5-ylamino)-1H-indole;

5-(1-phenyltetraz-5-ylamino)-(2-dimethylaminoethyl)-1H-indole;

5-(3-nitropyrid-2-ylamino)-3-(piperid-4-yl)-1H-indole;

5-(3-nitropyrid-2-ylamino)-3-(1,2,5,6-tetrahydropyrid-4-yl)-1H-indole;

5-(5-nitropyrid-2-ylamino)-3-(1,2,5,6-tetrahydropyrid-4-yl)-1H-indole;

5-(3-nitropyrid-2-yloxy)-3-(1,2,5,6-tetrahydropyrid-4-yl)-1H-indole;

5-(5-nitropyrid-2-yloxy)-3-(1,2,5,6-tetrahydropyrid-4-yl)-1H-indole;

3-(2-dimethylaminoethyl)-5-(3-aminopyrid-2-ylamino)-1H-indole;

3-(2-dimethylaminoethyl)-5-(3-phenylcarbonylaminopyrid-2-ylamino)-1H-indole;

3-(2-dimethylaminoethyl)-5-(6-benzylaminocarbonyl-3-methylthio-1,2,4-triazin-5-ylamino)-1H-indole;

5-amino-3-(N-methylpyrrolidin-3-yl)-1H-indole;

(R)-5-amino-3-(N-methylpyrrolidin-2-ylmethyl)-1H-indole;

(R)-5-amino-3-(pyrrolidin-2-ylmethyl)-1H-indole;

The present invention also relates to a pharmaceutical composition for treating a condition selected from hypertension, depression, anxiety, eating disorders, obesity, drug abuse, cluster headache, migraine, pain, and chronic paroxysmal hemicrania and headache associated with vascular disorders comprising an mount of a compound of the formula I or a pharmaceutically acceptable salt thereof effective in treating such condition and a pharmaceutically acceptable carrier.

The present invention also relates to a method for treating a condition selected from hypertension, depression, anxiety, eating disorders, obesity, drug abuse, cluster headache, migraine, pain and chronic paroxysmal hemicrania and headache associated with vascular disorders comprising administering to a mammal (e.g., a human) requiring such treatment an amount of a compound of the formula I or a pharmaceutically acceptable salt thereof effective in treating such condition.

The present invention also relates to a method for treating disorders arising from deficient serotonergic neurotransmission (e.g., depression, anxiety, eating disorders, obesity, drug abuse, cluster headache, migraine, pain and chronic paroxysmal hemicrania and headache associated with vascular disorders) comprising administering to a mammal (e.g., a human) requiring such treatment an amount of a compound of the formula I or a pharmaceutically acceptable salt thereof effective in treating such condition.

The present invention also relates to a compound of the formula

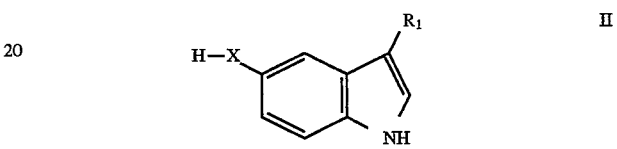

where X and $R_1$ are as defined for formula I. The compounds of formula II can be used, for example, as intermediates in preparing compounds of formula I.

DETAILED DESCRIPTION OF THE INVENTION

Compounds of formula I are prepared by the following reaction scheme

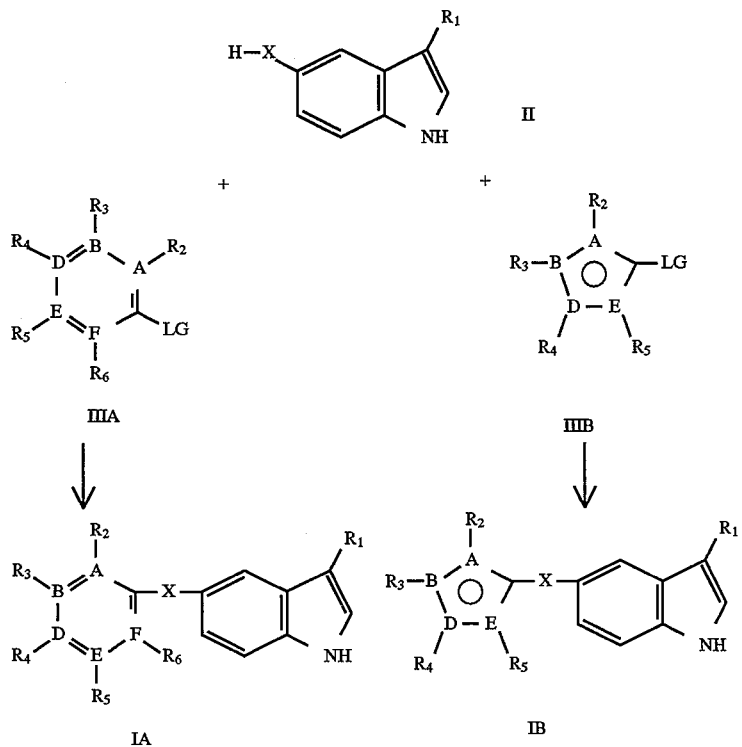

using a compound of formula II, where $R_1$ is as defined above for formula I, with a compound of formula IIIA or IIIB, where X, A, B, D, E, F, $R_2$, $R_3$, $R_4$, $R_5$, and $R_6$ are as defined above for formula I and where LG is a leaving group such as, for example, Cl, Br, I, SCH$_3$, SO$_2$CH$_3$, SPh, or SO$_2$Ph (Ph=phenyl). This reaction can be performed under acidic, basic, or neutral condition, usually at elevated temperatures. Suitable bases include sodium hydrogen carbonate, trialkylamines, sodium hydride, and sodium carbonate. Triethylamine is the preferred base. Suitable acids include mineral acids (e.g. hydrochloric and hydrobromic acid) and organic acids (e.g. acetic acid). The preferred acid is acetic acid. Suitable solvents include methanol, ethanol, dioxane, tetrahydrofuran, acetonitrile, and N,N-dimethylformamide. Ethanol is the preferred solvent. The reaction is usually conducted at a temperature of from about 50° C. to about 154° C., preferably about 70° C. to about 80° C.

Compounds of formula Ii can be prepared as outlined in the following:

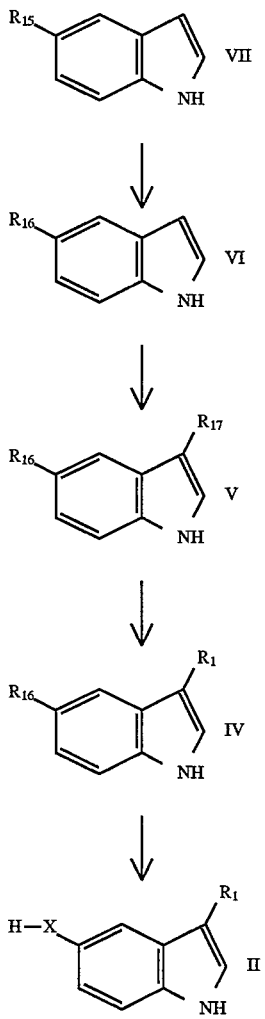

Compounds of formula VI where R$_{16}$ is a protected heteroatom group, such as, for example, —N(R$_{18}$)$_2$, —NHR$_{18}$, —OR$_{18}$, —SR$_{18}$, 2,5-dimethyl-1-H-pyrrole or —NO$_2$, and R$_{18}$ is hydrogen, benzoyl or benzyl are prepared by reacting a compound of formula VII where R$_{15}$ is —SH, —NH$_2$, —OH with benzyl or benzoyl halides (preferable benzyl bromide or benzoyl chloride) or acetyl acetone in the presence of a base in an inert solvent. Compounds of formula VII are either commercially available or can be produced using methods known to one skilled in the art.

Suitable bases include sodium bicarbonate, sodium carbonate, sodium hydride, and trialkylamines. Triethylamine is the preferred base. Suitable solvents include dimethylformamide, ethers (including tetrahydrofuran), and C$_1$–C$_3$ alcohols. Tetrahydrofuran is the preferred solvent. The reaction is usually conducted at a temperature of about 25° C. to about 100° C., preferably about 25° C.

Compounds of formula V can be prepared by reaction of a compound of formula VI where R$_{16}$ is as defined above for formula IV with an appropriate electrophile under acidic, basic, or neutral conditions. Suitable electrophiles include N-protected proline acid chlorides, N-protected-4-piperidones, oxalyl chloride, and maleimide. In the case of oxalyl chloride, the resulting indole-3-glyoxamic acid chloride is further reacted with a secondary amine of the formula NHR$_5$R$_6$ where R$_5$ and R$_6$ are as defined for formula I. Suitable acids include mineral acids, acetic acid, and formic acid. Suitable bases include Grignard reagents including ethyl magnesium bromide, primary, secondary or tertiary amines, sodium or potassium metal, or sodium hydride. Suitable solvents include ethers (including tetrahydrofuran and diethyl ether), benzene, toluene, acetic acid, formic acid, or C$_1$–C$_4$ alcohols. The reaction is usually conducted at a temperature from about 0° C. to 150° C., preferably in the range of about 0° C. to about 120° C. In the case where the electrophile is an N-protected proline acid chloride, the preferred solvent is benzene, the reaction is preferably run under basic conditions using ethyl magnesium bromide as the preferred base, and the reaction is run at a temperature preferably about 0° C. In the case where the electrophile is an N-protected-4-piperidone, the preferred solvent is methanol, the reaction is preferably run under basic conditions using sodium methoxide as the preferred base, and the reaction is run at a temperature preferably about 65° C. In the case where the electrophile is oxalyl chloride, the preferred solvent is ether, the reaction is preferably run under basic conditions using HNR$_5$R$_6$ as the preferred base, and the reaction is run at a temperature preferably about 0° C. In the case where the electrophile is a maleimide, the preferred solvent is acetic acid, the reaction is preferably run under acidic conditions using acetic acid as the preferred acid, and the reaction is run at a temperature preferably about 101° C.

Compounds of formula IV can be prepared from a compound formula V where R$_{17}$ is

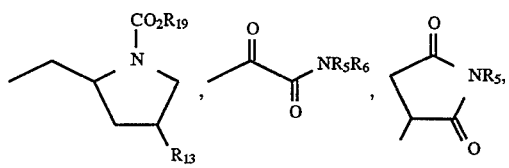

or

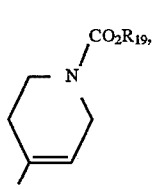

R$_5$ and R$_6$ are as defined above for formula I, R$_{16}$ is defined above for formula IV, and R$_{19}$ is t-butyl or benzyl via a hydride reduction in an Inert solvent. Suitable reducing agents include lithium aluminum hydride, lithium borohydride, and diborane. Lithium aluminum hydride is preferred. Suitable inert solvents include tetrahydrofuran, dioxane, and other ethers. Tetrahydrofuran is the preferred solvent. The reaction is usually conducted at a temperature of about 25° C. to about 100° C., preferably about 65° C.

Compounds of formula II can be prepared from compounds of formula IV via heteroatom deprotection using a transition metal catalyst and a hydrogen source or hydroxylamine hemihydrochloride. Suitable solvents include $C_1-C_4$ alcohols, ethyl acetate, acetone, and dimethylformamide. Ethanol is the preferred solvent. Suitable transition metal catalysts include palladium on carbon, palladium hydroxide on carbon, and platinum oxide. The preferred catalysts is palladium hydroxide on carbon. Suitable hydrogen sources Include hydrogen gas, ammonium formate, and formic acid. Hydrogen gas is preferred, usually at a pressure of 1 to 3 atmospheres, preferably at 3 atmospheres pressure. The reaction is usually conducted at a temperature of about 25° C. to about 100° C., preferably about 40° C.

Compounds of formula VII are commercially available.

Compounds of formula II can also be produced using methods known to one skilled in the art, such as, for example, the protocols in Shaw, E. and Woolley, D. W., J. Am. Chem. Soc., 1877 (1953) or those described in Example 9, Example 12, Example 14, Example 16, Example 17, Example 21, or Example 25. Compounds of formula III are either commercially available or can be produced using methods known to one skilled in the art.

Compounds of formula I are also prepared by the alkylation of a compound of formula

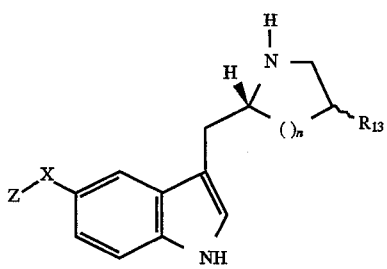

wherein Z, X, and n are as defined above with an alkylating agent and a base in an inert solvent. Suitable alkylating agents include alkyl halides (chlorides, bromides, or iodides), alkyl tosylates, alkyl mesylates, alkyl triflates, α, β-unsaturated ketones, α,β-unsaturated esters, α,β-unsaturated amides, and α,β-unsaturated nitriles, depending on the desired $R_7$ group. Alkyl halides (iodides) are preferred. Suitable solvents include methylene chloride, chloroform, carbon tetrachloride, acetonitrile, tetrahydrofuran, diethyl ether, dioxane, N,N-dimethylformamide, ethanol, propanol, methanol. The preferred solvent is acetonitrile. The reaction is generally conducted between a temperature of about 0° C., to about 150° C. preferably about 25° C. to about 65° C.

Unless indicated otherwise, the pressure of each of the above reactions is not critical. Generally, the reactions will be conducted at a pressure of about one to about three atmospheres, preferably at ambient pressure (about one atmosphere).

The compounds of the formula I which are base in nature are capable of forming a wide variety of different salts with various inorganic and organic acids. Although such salts must be pharmaceutically acceptable for administration to animals, it is often desirable in practice to initially isolate a compound of the formula I from the reaction mixture as a pharmaceutically unacceptable salt and then simply convert the latter back to the free base compound by treatment with an alkaline reagent, and subsequently convert the free be to a pharmaceutically acceptable acid addition salt. The acid addition salts of the be compounds of this invention are readily prepared by treating the base compound with a substantially equivalent amount of the chosen mineral or organic acid in an aqueous solvent medium or in a suitable organic solvent such as methanol or ethanol. Upon careful evaporation of the solvent, the desired solid salt is obtained.

The acids which are used to prepare the pharmaceutically acceptable acid addition salts of the base compounds of this invention are those which form non-toxic acid addition salts, i.e., salts containing pharmacologically acceptable anions, such as hydrochloride, hydrobromide, hydroiodide, nitrate, sulfate or bisulfate, phosphate or acid phosphate, acetate, lactate, citrate or acid citrate, tartrate or bitartrate, succinate, maleate, fumarate, gluconate, saccharate, benzoate, methanesulfonate and pamoate [i.e., 1,1'-methylene-bis-(2-hydroxy-3-naphthoate)] salts.

Those compounds of the formula I which are also acidic in nature, e.g., where Z contains a carboxylate, are capable of forming base salts with various pharmacologically acceptable cations. Examples of such salts include the alkali metal or alkaline-earth metal salts and particularly, the sodium and potassium salts. These salts are all prepared by conventional techniques. The chemical bases which are used as reagents to prepare the pharmaceutically acceptable base salts of this invention are those which form non-toxic base salts with the herein described acidic compounds of formula I. These non-toxic base salts include those derived from pharmacologically acceptable cations such as, for example, sodium, potassium calcium and magnesium. These salts can easily be prepared by treating the corresponding acidic compounds with an aqueous solution containing the desired pharmacologically acceptable cations, and then evaporating the resulting solution to dryness, preferably under reduced pressure. Alternatively, they may also be prepared by mixing lower alkanolic solutions of the acidic compounds and the desired alkali metal alkoxide together, and then evaporating the resulting solution to dryness in the same manner as before. In either case, stoichiometric quantities of reagents are preferably employed in order to ensure completeness of reaction of as well as maximum product of yields of the desired final product.

The compounds of the formula I and the pharmaceutically acceptable salts thereof (hereinafter, also referred to as the active compounds of the invention) are useful psychotherapeutics and are potent serotonin (5-$HT_1$) agonists and may be used in the treatment of depression, anxiety, eating disorders, obesity, drug abuse, cluster headache, migraine, chronic paroxysmal hemicrania and headache associated with vascular disorders, pain, and other disorders arising from deficient serotonergic neurotransmission. The compounds can also be used as centrally acting antihypertensives and vasodilators. The active compounds of the invention are evaluated as anti-migraine agents by testing the extent to which they mimic sumatriptan in contracting the dog isolated saphenous vein strip (P. P. A. Humphrey et al., Br. J. Pharmacol., 94, 1128 (1988)). This effect can be blocked by methiothepin, a known serotonin antagonist. Sumatriptan is known to be useful in the treatment of migraine and produces a selective increase in carotid vascular resistance in the anaesthetized dog. It has been suggested (W. Fenwick et al., Br. J. Pharmacol., 96, 83 (1989)) that this is the basis of its efficacy.

The compositions of the present invention may be formulated in a conventional manner using one or more pharmaceutically acceptable carriers. Thus, the active compounds of the invention may be formulated for oral, buccal, intranasal, parenteral (e.g., intravenous, intramuscular or subcutaneous) or rectal administration or in a form suitable for administration by inhalation or insufflation.

For oral administration, the pharmaceutical compositions may take the form of, for example, tablets or capsules prepared by conventional means with pharmaceutically acceptable excipients such as binding agents (e.g. pregelatinised maize starch, polyvinylpyrrolidone or hydroxypropyl methylcellulose); fillers (e.g. lactose, microcrystalline cellulose or calcium phosphate); lubricants (e.g. magnesium stearate, talc or silica); disintegrants (e.g. potato starch or sodium starch glycolate); or wetting agents (e.g. sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g. sorbitol syrup, methyl cellulose or hydrogenated edible fats); emulsifying agents (e.g. lecithin or acacia); non-aqueous vehicles (e.g. almond oil, oily esters or ethyl alcohol); and preservatives (e.g. methyl or propyl p-hydroxybenzoates or sorbic acid).

For buccal administration the composition may take the form of tablets or lozenges formulated in conventional manner.

The active compounds of the invention may be formulated for parenteral administration by injection, including using conventional catheterization techniques or infusion. Formulations for injection may be presented in unit dosage form e.g. in ampules or in multi-dose containers, with an added preservative. The compositions may take such forms as suspensions, solutions or emulsions in oily or aqueous vehicles, and may contain formulating agents such as suspending, stabilizing and/or dispersing agents. Alternatively, the active ingredient may be in powder form for reconstitution with a suitable vehicle, e.g. sterile pyrogen-free water, before use.

The active compounds of the invention may also be formulated in rectal compositions such as suppositories or retention enemas, e.g., containing conventional suppository bases such as cocoa butter or other glycerides.

For intranasal administration or administration by Inhalation, the active compounds of the invention are conveniently delivered in the form of a solution or suspension from a pump spray container that is squeezed or pumped by the patient or as an aerosol spray presentation from a pressurized container or a nebulizer, with the use of a suitable propellant, e.g. dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount. The pressurized container or nebulizer may contain a solution or suspension of the active compound. Capsules and cartridges (made, for example, from gelatin) for use in an inhaler or insufflator may be formulated containing a powder mix of a compound of the invention and a suitable powder base such as lactose or starch.

A proposed dose of the active compounds of the invention for oral, parenteral or buccal administration to the average adult human for the treatment of the conditions referred to above (e.g., migraine) is 0.1 to 200 mg of the active ingredient per unit dose which could be administered, for example, 1 to 4 times per day.

Aerosol formulations for treatment of the conditions referred to above (e.g., migraine) in the average adult human are preferably arranged so that each metered dose or "puff" of aerosol contains 20 µg to 1000 µg of the compound of the invention. The overall daily dose with an aerosol will be within the range 100 µg to 10 mg. Administration may be several times daily, for example 2, 3, 4 or 8 times, giving for example, 1, 2 or 3 doses each time.

The following non-limiting Examples illustrate the preparation of the compounds of the present invention. Melting points are uncorrected. NMR data are reported in parts per million ($\delta$) and are referenced to the deuterium lock signal from the sample solvent. Specific rotations were measured at room temperature using the sodium D line (589 nm). Unless otherwise stated, all mass spectrum were performed using electron impact (EI, 70 eV) conditions.

Commercial reagents were utilized without further purification. Chromatography refers to column chromatography performed using 32–63 µm silica gel and executed under nitrogen pressure (flash chromatography) conditions. Room temperature refers to 20°–25° C.

EXAMPLE 1

General Method for the Synthesis of 5-Arylamino-1H-indoles via the Condensation of a 5-Aminoindole Derivative with a Haloarene A solution of the 5-aminoindole (2.00 mmol), the haloarene (3.00 mmol, 1.5 eq), and a base (if needed, 3.00 mmol) in an appropriate anhydrous solvent (10 mL) was either heated at reflux under nitrogen for 1–18 hours, depending on substrate, or stirred at room temperature for 1 hour, depending on substrate. The reaction was cooled and then directly chromatographed using silica gel (approximately 50 g) and elution with methylene chloride: methanol: ammonium hydroxide [9:1:0.1] to afford the 5-arylamino-1H-indole derivative. In some case recrystallization of the solid obtained from chromatography was performed to obtained analytically pure samples of the title compound.

Following this procedure the following compounds were prepared.

A. 3-(2-Dimethylaminoethyl)-5-(3-nitropyrid-2-ylamino)-1H-indole

5-Amino-3-(2-dimethylaminoethyl)indole [Shaw, E. and Woolley, D. W., *J. Am. Chem. Soc.*, 1877 (1953)] and 2-chloro-3-nitropyridine were used. Triethylamine was used as base, p-dioxane was used as solvent, and the reaction was heated at reflux (101° C.) for 3 hours. Chromatography afforded the title compound (67%) as a dark red foam: mp, 59.0°–61.0° C.; $^1$H NMR (CDCl$_3$) $\delta$8.66 (br s, 1H), 8.51 (dd, J=8.3 and 1.8 Hz, 1H), 8.41 (dd, J=4.4 and 1.8 Hz, 1H), 7.76 (br s, 1H), 7.30–7.24 (m, 2H), 6.97(d, J=2.1 Hz, 1H), 6.73 (dd, J=8.3 and 4.4 Hz, 1H), 2.97–2.91 (m, 2H), 2.70–2.63 (m, 2H), 2.36 (s, 6H); $^{13}$C NMR (CDCl$_3$) $\delta$155.7, 151.5, 135.5, 134.5, 129.4, 128.2, 127.9, 122.8, 119.3, 114.4, 114.3, 113.0, 111.5, 60.3, 45.4, 23.7. Anal. calcd. for C$_{17}$N$_{19}$O$_2$.1/3H$_2$O: C, 61.62; H, 5.98; N, 21.13. Found: C, 61.53; H, 5.65; N, 20.80.

B. 3-(2-Dimethylaminoethyl)-5-(2-nitrophenylamino)-1H-indole

5-Amino-3-(2-dimethylaminoethyl)indole and 2-fluoronitrobenzene were used. Pyridine was used as base, bromobenzene was used as solvent, and the reaction was heated at reflux (156° C.) for 11 hours. Chromatography afforded the title compound (82%) as a dark red solid: mp, 116.0°–117.0° C.; $^{13}$C NMR (CD$_3$OD) $\delta$146.7, 136.7, 133.2, 131.0, 129.5, 127.2, 124.7, 121.3, 117.3, 117.2, 117.0, 114.1,113.4, 61.4, 45.4, 24.2; HRMS calculated for $C_{18}H_{20}N_4O_2$ 324.1588, found 324.1564. Anal. calcd. for $C_{18}H_{20}N_4O_2 \cdot 1/3H_2O$: C, 65.44; H, 6.31; N, 16.96. Found: 65.44; H, 5.92; N, 16.69.

C. 3-(2-Dimethylaminoethyl)-5-(3,5-dinitropyrid-2-ylamino)-1H-indole

5-Amino-3-(2-dimethylaminoethyl)indole and 2-chloro-3,5-dinitropyridine were used. Triethylamine was used as base, tetrahydrofuran was used as solvent, and the reaction was stirred at room temperature for 1 hour. Direct filtration of the reaction mixture afforded a red solid which was recrystallized in ethanol to afford the title compound (7%) as a red solid: mp, 194.0°–195.0° C.; $^{13}$C NMR (DMSO-d$_6$) δ152.2, 150.7, 134.7, 134.1, 131.2, 128.2, 127.1, 126.7, 123.9, 119.1, 114.8, 112.7, 111.4, 59.7, 44.9, 22.8; HRMS calculated for $C_{17}H_{18}N_6O_4$ 370.1391, found 370.1358. Anal. calcd. for $C_{17}H_{18}N_6O_4 \cdot 1/2H_2O$: C, 53.82; H, 5.04; N, 22.15. Found: C, 53.55; H, 4.58; N, 21.98.

D. 3-(2-Dimethylaminoethyl)-5-(3-aminocarbonylpyrid-2-ylamino)-1H-indole

5-Amino-3-(2-dimethylaminoethyl)indole and 2-chloronicotinamide were used. Pyridine was used as base, bromobenzene was used as solvent, and the reaction was heated at reflux (156° C.) for 18 hours. Chromatography followed by recrystallization (methanol/water) of the resulting solid in afforded the title compound (36%) as a yellow solid: mp, 127.0°–129.0° C.; $^{13}$C NMR (CD$_3$OD) δ173.0, 157.9, 152.2, 139.0, 135.4, 132.4, 129.0, 123.9, 119.1, 113.7, 113.2, 113.0, 112.5, 111.3, 61.4, 45.4, 24.3; HRMS calculated for $C_{18}H_{21}N_5O$ 323.1748, found 323.1726. Anal. calcd. for $C_{18}H_{21}N_5O \cdot H_2O$; C, 63.33; H, 6.79; N, 20.51. Found: C, 63.19; H, 6.50; N, 20.30.

E. 3-(2-Dimethylaminoethyl)-5-(2,6-dinitrophenylamino)-1H-indole

5-Amino-3-(2-dimethylaminoethyl)indole and 1-chloro-2,6-dinitrobenzene were used. Triethylamine was used as base, tetrahydrofuran was used as solvent, and the reaction was stirred at room temperature for 1 hour. Chromatography afforded the title compound (57%) as a dark red solid: mp, 187.0°–188.0° C.; $^{13}$C NMR (DMSO-d$_6$) δ139.9, 135.2, 134.0, 132.0, 131.8, 127.2, 123.8, 117.0, 115.4, 112.9, 112.0, 109.3, 59.9, 45.1, 23.0; HRMS calculated for $C_{18}H_{19}N_5O$ 369.1439, found 369.1428. Anal. calcd. for $C_{18}H_{19}N_5O$: C, 58.53; H, 5.18; N, 18.96. Found: C, 58.45; H, 4.96; N, 18.63.

F. 3-(2-Dimethylaminoethyl)-5-(2-cyanophenylamino)-1H-indole

5-Amino-3-(2-dimethylaminoethyl)indole and 2-fluorobenzonitrile were used. Pyridine was used as base, 2-fluorobenzonitrile was used as solvent, and the reaction was stirred at reflux for 8 hours. Chromatography afforded the title compound (2%) as a clear, pale brown oil: $^1$H NMR (CD$_3$OD) δ7.43 (dd, J=7.7 and 1.5 Hz, 1H), 7.38 (d, J=1.9 Hz, 1H), 7.34 (d, J=8.6 Hz, 1H), 7.30–7.23 (m, 1H), 7.07 (s, 1H) 6.97 (dd, J=8.6 and 1.9 Hz, 1H), 6.85 (d, J=8.5 Hz, 1H), 6.73–6.67 (m, 1H), 4.91 (s, 2H), 2.92–2.86 (m, 2H), 2.65–2.59 (m, 2H), 2.30 (s, 6H); HRMS calculated for $C_{19}H_{20}N_4$ 304.1690, found 304.1682.

G. 3-(2-Dimethylaminoethyl)-5-(3-trifluoromethylpyrid-2-ylamino)-1H-indole

6-Amino-3-(2-dimethylaminoethyl)indole and 2-chloro-3-trifluoromethylpyridine were used. Pyridine was used as base, N,N-dimethylformamide was used as solvent, and the reaction was heated at reflux (153° C.) for 18 hours. Chromatography afforded the title compound (10%) as a clear, pale brown oil: $^{13}$C NMR (CD$_3$OD) δ155.4, 152.3, 136.9, 136.1, 131.7, 129.0, 124.0, 120.9, 115.7, 113.9, 113.5, 112.5, 110.5, 61.4, 45.4, 24.3; LRMS (m/z, relative intensity) 348 (100, M$^+$), 303 (16), 290 (28), 268 (11), 250 (20); HRMS calculated for $C_{18}H_{19}F_3N_4$ 348.1564, found 348.1532.

H. 3-(2-Dimethylaminoethyl)-5-(2,4-dinitrophenylamino)-1H-indole

5-Amino-3-(2-dimethylaminoethyl)indole and 1-chloro-2,4-dinitrobenzene were used. Triethylamine was used as base, tetrahydrofuran was used as solvent, and the reaction was stirred at room temperature for 2 hours. Chromatography afforded the title compound (73%) as a dark red solid: mp, 177.0°–179.0° C.; $^{13}$C NMR (DMSO-d$_6$) δ148.2, 135.6, 135.2, 130.1, 129.6, 128.2, 127.9, 124.3, 123.5, 119.6, 116.9. 116.3, 113.3, 112.5, 60.0, 45.2, 23.0; FAB HRMS calculated for $C_{18}H_{19}N_5O_4$.[H$^+$]370.1517, found 370.1492.

I. (R)-5-(3-Nitropyrid-2-ylamino)-3-(pyrrolidin-2-ylmethyl)-1H-indole (R)-5-Amino-3-(pyrrolidin-2-ylmethyl)indole and 2-chloro-3-nitropyridine. Sodium acetate was used as base, acetic was used as solvent, and the reaction was heated at reflux (116° C.) for 2 hours. Column chromatography afforded the title compound (23%) as a dark red foam: $^1$H NMR (CDCl$_3$) δ10.05 (br s, 1H), 9.23 (br s, 1H), 8.49 (dd, J=1.8 and 8.3 Hz, 1H), 8.39 (1.8 and 4.5 Hz, 1H), 7.70 (d, J=1.7 Hz, 1H) 7.33–7.22 (m, 2H), 6.98 (s, 1H), 6.73 (dd, J=4.5 and 8.3 Hz, 1H), 3.46–3.34 (m, 1H), 310– 2.97 (m, 1H), 2.97–2.78 (m, 3H), 1.99–1.64 (m, 3H), 1.56–1.42 (m, 1H); $^{13}$C NMR (CDCl$_3$) δ155.7, 151.5, 135.5, 134.5, 129.2, 128.1, 127.8, 123.8, 119.4, 114.3, 113.0, 111.6, 59.5, 45.7, 31.3, 30.6, 24.7; FAB LRMS (m/z, relative intensity) 338 (6,[MH$^+$]), 309 (12), 155 (49), 135 (38), 119 (100). Anal. calcd. for $C_{18}H_{19}N_5O_2 \cdot 0.67 C_2H_4O_2$ [acetic acid]: C, 61.53; H, 5.79; N, 18.56. Found: C, 61.57; H, 5.74; N, 18.82.

J. (R)-3-(N-Methylpyrrolidin-2-ylmethyl)-5-(3-nitropyrid-2-ylamino)-1H-indole (R)-3-(N-Methylpyrrolidin-2-ylmethyl)indole and 2-chloro-3-nitropyridine were used. Triethylamine was used as base, acetonitrile was used as solvent, and the reaction was heated at reflux for 3.5 hours. Chromatography afforded the title compound (81%) as a dark red foam: $^1$H NMR (CDCl$_3$) δ10.11 (br s, 1H), 8.52 (dd, J=1.7 Hz, J=1.8 and 8.4 Hz, 1H), 8.43 (1.8 and 4.5 Hz; 1H), 8.33 (br s, 1H), 7.77 (d, 1H), 7.35 (d, J=8.7 Hz, 1H), 7.26 (dd, J=2.0 and 8.6 Hz, 1H), 7.03 (d, J=2.1 Hz, 1H), 6.74 (dd, J=4.44 and 8.4 Hz, 1H), 3.21–3.12 (m, 2H), 2.68–2.58 (m, 1H), 2.54–2.46 (m, 1H), 2.47 (s, 3H), 2.28–2.18 (m, 1H), 1.89–1.73 (m, 2H), 1.73–1.54 (m, 2H); $^{13}$C NMR (CDCl$_3$) δ155.7, 151.5, 135.5, 134.3, 129.5, 128.2, 128.1, 123.1, 119.4, 114.3, 113.0, 111.4, 66.7, 57.5, 40.8, 31.5, 29.9, 21.9, Anal. calcd. for $C_{19}H_{21}N_5O_2 \cdot 1/3H_2O$: C, 63.85; H, 6.11; N, 19.59. Found: C, 63.86; H, 5.86; N, 19.31.

K. 6-(3-(2-Dimethylaminoethyl)indol-5-ylamino)purine

5-Amino-3-(2-dimethylaminoethyl)indole and 6-chloropurine were used. No base was used, acetic acid was used as solvent, and the reaction was heated at reflux (116° C.) for 15 hours. Chromatography afforded the title compound (66%) as a white foam: mp, decomposes 175° C.; $^{13}$C NMR (CD$_3$OD) δ153.7, 153.4, 141.5, 136.0, 131.5, 128.3, 125.6, 119.2, 113.3, 113.0, 109.9, 59.1, 43.6, 21.9. Anal. calcd for $C_{17}H_{19}N_7 \cdot HCl \cdot 2H_2O$: C, 51.84; H, 6.14; N, 24.89. Found: C, 52.14; H, 6.22; N, 25.03.

L. (R,S)-3-(N-Methylpyrrolidin-3-yl)-5-(3-nitropyrid-2-ylamino)-1H-indole (R,S)-3-(N-Methylpyrrolidin-3-yl)indole and 2-chloro-3-nitropyridine were used. Sodium acetate was used as base, acetic acid was used as solvent, and the reaction was heated at reflux for 4 hours. Chromatography afforded the title compound (44%) as a dark red foam: mp, 55.0°–57.0° C.; $^{13}$C NMR (CDCl$_3$) δ155.7, 151.5, 135.5, 135.0, 129.0, 128.1, 127.1, 121.7, 119.3, 119.2, 114.7, 113.0, 111.6, 62.8, 56.2, 42.4, 35.1, 32.1; FAB LRMS (m/z, relative intensity) 306 (MH$^+$, 100), 155 (38). Anal. calcd. for C$_{18}$H$_{19}$N$_5$O$_2$.1/2 C$_4$H$_4$O$_2$ [ethyl acetate]: C, 62.98; H, 6.08; N, 18.36. Found: C, 62.71; H, 5.80; N, 18.51.

M. 3-(2-Dimethylaminoethyl)-5-(6-ethoxycarbonyl-3-methylthio-1,2,4-triazin-5-ylamino)-1H-indole 5-Amino-3-(2-dimethylaminoethyl)indole and 6-carbethoxy-5-chloro-3-methylthio-1,2,4-triazine [Pesson, M. et al., *Eur. J. Med. Chem.*, 269 (1972)] were used. Triethylamine was used as base, tetrahydrofuran was used as solvent, and the reaction was stirred at room temperature for 1 hour. Chromatography afforded the title compound (53%) as an orange solid: mp, 197.0°–199.0° C. with effervescence; $^{13}$C NMR (DMSO-d$_6$) δ173.2, 165.5, 150.5, 133.9, 132.5, 127.7, 127.1, 123.9, 116.8, 113.0, 112.2, 111.5, 62.0, 60.0, 45.2, 23.1, 14.0, 13.2; LRMS (m/z, relative intensity) 400 (M$^{3O}$, 11 ), 386 (5), 195 (11), 163(13), 58 (100). Anal. calcd. for C$_{19}$H$_{24}$N$_6$O$_2$S.0.3 H$_2$O: C, 56.22 ; H, 6.11; N, 20.70. Found: C, 55.50; H, 5.89; N, 20.33.

N. 5-(Benzoxaz-2-ylamino)-3-(2-dimethylaminoethyl)-1H-indole

5-Amino-3-(2-dimethylaminoethyl)indole and 2-chlorobenzoxazole were used. No base was used, acetic acid was used as solvent, and the reaction was stirred at reflux (116° C.) for 2 hours. Chromatography afforded the title compound (24%) as a pale yellow foam: $^{13}$C NMR (CDCl$_3$) δ160.5, 148.1, 142.7, 133.8, 130.0, 127.8, 124.0, 123.1, 121.0, 116.4, 116.4, 113.6, 111.8, 110.6, 108.9, 60.1, 45.3, 23.4; LRMS (m/z, relative intensity) 320 (M$^+$, 33), 262 (15), 101 (12), 86 (33), 58 (100). Anal. calcd. for C$_{19}$H$_{20}$N$_4$O.1/4 H$_2$O: C, 70.23; H, 6.36; N, 17.24. Found: C, 70.53; H, 6.46; N, 17.06.

O. 5-(1-Phenyltetraz-5-ylamino)-(2-dimethylaminoethyl)-1H-indole

5-Amino-3-(2-dimethylaminoethyl)indole and 5-chloro-1-phenyl-1H-tetrazole were used. Sodium carbonate was used as base, absolute ethanol was used as solvent, and the reaction was heated at reflux (78° C.) for 48 hours. Chromatography followed by trituration of the chromatographic residue with chloroform afforded the title compound (7%) as a white solid: mp, 187.0°–188.0° C.; $^1$H NMR (CD$_3$OD) δ7.73 (d, J=1.9, 1H), 7.56–7.52 (m, 3H), 7.29–7.22 (m, 3H), 7.20 (dd, J=2.0 and 8.6 Hz, 1H), 6.98–6.95 (m, 1H), 4.93 (s, 2H), 2.96–2.91 (m, 2H), 2.66–2.59 (m, 2H), 2.27 (s, 6H); FAB LRMS (m/z, relative intensity) 348 (MH$^+$, 100), 309 (23); HRMS calculated for C$_{19}$H$_{21}$N$_7$ 347.1861, found 347.1867. Anal. calcd. for C$_{19}$H$_{21}$N$_7$.2/3 CHCl$_3$ [chloroform]: C, 55.33; H, 4.64; N, 22.96. Found: C, 55.5; H, 4.94; N, 23.33.

P. 5-(3-Benzylthio-1,2,4-thiadiaz-5-ylamino)-3-(N-methylpyrrolidin-2-ylmethyl)-1H-indole (R)-5-Amino-3-(N-methylpyrrolidin-2-ylmethyl)-1H-indole and 3-benzylthio-5-chloro-1,2,4-thiadiazole were used. Sodium acetate was used as base, acetic acid was used as solvent, and the reaction was heated at reflux for 1.5 hours. Column chromatography afforded the title compound (9%) as an amorphous solid: $^1$H NMR (CD$_3$OD) δ7.67 (br s, 1H), 7.40–7.17 (m, 6H), 7.09 (s, 1H), 7.04 (dd, J=8.6 and 2.1 Hz, 1H), 4.88 (br s, approx 3H), 4.40 (s, 2H), 3.16–3.03 (m, 2H), 2.60–2.37 (m, 2H), 2.43 (s, 3H), 2.25–2.19 (m, 1H), 1.83–1.50 (m, 4H); $^{13}$C NMR (CD$_3$OD) δ169.0, 139.1, 135.7, 133.1, 130.1, 129.5, 129.2, 128.3, 125.3, 116.3, 113.8, 113.2, 110.8, 68.4, 58.3, 41.1, 36.8, 32.4, 30.4, 22.4. HRMS calculated for C$_{23}$H$_{25}$N$_5$S$_2$ 435.1555, found 435.1518. Anal. calcd for C$_{23}$H$_{25}$N$_5$S$_2$.0.4 NH$_3$: C, 62.50; H, 5.75; N, 17.11. Found C, 62.93; H, 5.50; N, 17.57.

Q. 3-(2-Dimethylaminoethyl)-5-(pyrimid-2-ylamino)-1H-indole

5-Amino-3-(2-dimethylaminoethyl)-1H-indole and 2-chloropyrimidine were used. Sodium acetate was used as base, acetic acid was used as solvent, and the reaction was heated at reflux for 12 hours. Column chromatography afforded the title compound (11%) as a yellow solid: $^{13}$C NMR (CD$_3$OD) δ162.6, 159.2, 135.4, 132.2, 128.9, 124.0, 118.6, 113.7, 112.6, 112.4, 112.3, 61.3, 45.4, 24.3; HRMS calculated for C$_{16}$H$_{19}$N$_5$ 281.1642, found 281.1660. Anal. calcd for C$_{16}$H$_{19}$N$_5$.0.5C$_2$H$_4$O$_2$[acetic acid]: C, 65.62; H, 6.80; N, 22.51. Found: C, 65.74; H, 6.68; N, 22.60.

R. 3-(2-Dimethylaminoethyl)-5-(3-methylsulfonylpyrid-2-ylamino)-1H-indole

5-Amino-3-(2-dimethylaminoethyl)-1H-indole and 2-chloro-3-methylsulfonylpyridine were used. 2,6-Lutidine was used as base, bromobenzene was used as solvent, and the reaction was heated at reflux for 3.5 hours. Column chromatography afforded the title compound (13%) as a yellow solid: top, 66.0°–68.0° C.; $^1$H NMR (CDCl$_3$) δ8.46 (s, NH), 8.33 (dd, J=4.8 and 1.9 Hz, 1H), 8.33 (br s, NH), 8.06 (dd, J=7.8 and 1.9 Hz, 1H), 7.66 (d, J=1.8 Hz, 1H), 7.29 (d, J=8.5 Hz, 1), 7.20 (dd, J=8.6 and 2.0 Hz, 1H), 6.97 (d, J=2.2 Hz, 1H), 6.78 (dd, J=7.8 and 4.8 Hz, 1H), 3.15 (s, 3H), 2.94–2.88 (m, 2H), 2.68–2.60 (m, 2H), 2.34 (s, 6H); HRMS calculated for C$_{18}$H$_{22}$N$_4$O$_2$S 358.1459, found 358.1490.

S. 3-1N-Methylpyrrolidin-2-ylmethyl)-5-(2-nitrophenylamino)-1H-indole (R)-5-Amino-3-(N-methylpyrrolidin-2-ylmethyl)-1H-indole and were used. Triethylamine was used as base, o-nitrofluorobenzene was used as solvent, and the reaction was heated at reflux for 24 hours. Column chromatography afforded the title compound (48%) as a red amorphous solid: $^1$H NMR (CDCl$_3$) δ9.62 (br s, NH), 8.77 (br s, NH), 8.19 (dd, J=8.7 and 1.5 Hz, 1H), 7.47 (d, J=1.6 Hz, 1H), 7.38 (d, J=8.5 Hz, 1H), 7.29–7.23 (m, 1H), 7.09–7.00 (m, 3H), 6.69–6.64 (m, 1H), 3.20–3.12 (m, 2H), 2.63 (dd, J=14.0 and 9.5 Hz, 1H), 2.54–2.45 (m, 1H), 2.45 (s, 3H), 2.25 (dd, J=17.1 and 9.2 Hz, 1H), 1.91–1.54 (m, 4H); $^{13}$C NMR (CDCl$_3$) δ145.4, 135.7, 134.8, 132.1, 130.1, 128.6 126.5, 123.6, 120.7, 116.4, 116.4, 116.1, 114.1, 112.2, 66.7, 57.5, 40.8, 31.5, 29.8, 21.9; FAB HRMS calculated for [C$_{20}$H$_{22}$N$_4$O$_2$.H] 351.1823, found 351.1797.

T. 5-(6-Methoxy-3-nitropyrid-2-ylamino)-3-(N-methylpyrrolidin-2-ylmethyl)-1H-indole (R)-5-Amino-3-(N-methylpyrrolidin-2-ylmethyl)-1H-indole and 2-chloro-6-methoxy-3-nitropyridine were used. Triethylamine was used as base, absolute ethanol was used as solvent, and the reaction was heated at reflux for 5.5 hours. Column chromatography afforded the title compound (54%) as a red amorphous solid: $^1$H NMR (CDCl$_3$) δ8.80 (br s, NH), 8.37 (d, J=9.1 Hz, 1H), 7.85 (s, 1H), 7.34–7.28 (m, 7.03) (d, J=2.0 Hz, 1H), 6.14 (d, J=9.1 Hz, 1H), 3.85 (s, 3H), 3.19–3.11 (m, 2H) (dd, J=13.8 and 9.5 Hz, 1H), 2.54–2.45 (m, 1H), 2.45 (s, 3H), 2.24 (dd, J=17.1 and 9.3 Hz, 1H), 1.91–1.54 (m, 4H); $^{13}$C NMR (CDCl$_3$) δ166.9, 151.3, 138.2, 134.0, 129.6, 127.8, 123.3, 122.0, 118.6, 114.1, 113.3, 111.1, 102.0, 66.5, 57.5, ,54.7, 40.8, 31.6, 29.9, 21.9; HRMS calculated for C$_{20}$H$_{23}$N$_5$O$_3$ 381.1 803, found 381.1799.

U. 5-(4-Methyl-3-nitropyrid-2-ylamino)-3-(N-methylpyrrolidin-2-ylmethyl)-1H-indole (R)-5-Amino-3-(N-methylpyrrolidin-2-ylmethyl)-1H-indole and 2-chloro-4-methyl-3-nitropyridine were used.

Triethylamine was used as base, absolute ethanol was used as solvent, and the reaction was heated at reflux for 24 hours. Column chromatography afforded the title compound (34%) as a red amorphous solid: $^1$H NMR (CDCl$_3$) δ9.26 (brs, NH),8.79 (brs, NH),8.10 (d,J=4.8 Hz, 1H), 7.64(d,J=1.7 Hz, 1H), 7.29 (d, J=8.5 Hz, 1H), 7.17 (dd, J=8.5 and 1.9 Hz, 1H), 6.97 (d, J=2.2 Hz, 1H), 6.56 (d, J=4.8 Hz, 1H), 3.25–3.16 (m, 2H), 2.67 (dd, J=13.2 and 9.4 Hz, 1H), 2.64–2.56 (m, 1H), 2.56 (s, 3H), 2.46 (s, 3H), 2.30 (dd, J=17.7 and 9.4 Hz, 1H), 1.90–1.60 (m, 4H); $^{13}$C NMR (CDCl$_3$) δ152.2, 151.5, 146.6, 134.3, 131.0, 130.0, 127.9, 123.4, 119.4, 117.1, 114.0, 113.3, 111.6, 67.0, 57.4, 40.7, 31.4, 29.5, 21.8, 21.7; FAB HRMS calculated for [C$_{20}$H$_{23}$N$_5$O$_2$.H]366.1932, found 366.1957.

V. 3-(N-Methylpyrrolidin-2-ylmethyl)-5-(3-nitro-5-phenylpyrid-2-ylamino)-1H-indole (R)-5-Amino-3-(N-methylpyrrolidin-2-ylmethyl)-1H-indole and 4-bromo-3-nitrobiphenyl were used. Triethylamine was used as base, N,N-dimethylformamide was used as solvent, and the reaction was heated at 110° C. for 12 hours. Column chromatography afforded the title compound (24%) as a red amorphous solid: $^1$H NMR (CDCl$_3$) δ9.63 (br s, NH), 8.97 (br s, NH), 8.42 (d, J=2.2 Hz, 1H), 7.56–7.25 (m, 9H), 7.08 (d, J=9.0 Hz, 2H), 3.50–3.32 (m, 2H), 2.95–2.79 (m, 2H), 2.59–2.52 (m, 1H), 2.53 (s, 3H), 2.05–1.71 (m, 4H); $^{13}$C NMR (CDCl$_3$) δ144.4, 138.8, 134.9, 134.5, 132.4, 131.1, 130.2, 129.7, 129.0, 127.3, 126.2, 124.7, 124.1, 120.8, 116.7, 115.9, 112.7, 112.0, 67.9, 57.4, 40.6, 31.2, 28.6, 21.9; FAB HRMS calculated for [C$_{26}$H$_{26}$N$_4$O$_2$.H]427.2136, found 427.2099.

W. 5-(3-Cyanopyrid-2-ylamino)-3-(N-methylpyrrolidin-2-ylmethyl)-1H-indole (R)-5-Amino-3-(N-methylpyrrolidin-2-ylmethyl)-1H-indole and 2-chloronicotinonitrile were used. Sodium carbonate were used as base. N,N-dimethylformamide was used as solvent, and the reaction was heated at 110° C. for 20 hours. Column chromatography afforded the title compound (32%) as an orange amorphous solid: R$_f$=0.4 in 9:1:0.1 [methylene chloride/methanol/ammonium hydroxide]; $^{13}$C NMR (CDCl$_3$) δ157.7, 152.7, 141.7, 134.2, 129.8, 128.1, 123.1, 122.2, 118.7, 116.8, 113.6, 113.2, 111.5, 102.2, 66.6, 57.4, 40.8, 31.5, 30.0, 21.9; FAB HRMS calculated for [C$_{20}$H$_{21}$N$_5$.H]332.2073, found 332.1871.

X. 5-(6-isopropoxy-3-nitropyrid-2-ylamino)-3-(N-methylpyrrolidin-2-ylmethyl)-1H-indole (R)-5-Amino-3-(N-methylpyrrolidin-2-ylmethyl)-1H-indole and 2,6-dichloro-3-nitropyridine were used. No base was used, and 2-propanol was used as solvent. This reaction mixture was stirred at room temperature was 1 hour. Then a solution of sodium hydride (5 eq) in 2-propanol was added dropwise to the above reaction mixture with cooling at 0° C. The resulting reaction mixture was stirred at room temperature under nitrogen for 2.5 hours. The reaction mixture was then evaporated under reduced pressure. Column chromatography of the residue afforded the title compound (42%) as an orange amorphous solid: $^1$H NMR (CDCl$_3$) δ10.6 (br s, NH), 8.57 (br s, NH), 8.37 (d, J=9.2 Hz, 1H), 7.71 (s, 1H), 7.34–7.28 (m, 2H), 7.05 (d, J=2.0 Hz, 1H), 6.08 (d, J=9.2 Hz, 1H), 5.14 (sept, J=6.2 Hz, 1H), 3.18–3.10 (m, 2H), 2.61 (dd, J=14.0 and 9.4 Hz, 1H), 2.54–2.45 (m, 1H), 2.44 (s, 3H), 2.23 (dd, J=17.2 and 9.3 Hz, 1H), 1.90–1.53 (m, 4H), 1.25 (d, J=6.1 Hz, 3H), 1.24 (d, J=6.2 Hz, 3H); $^{13}$C NMR (CDCl$_3$) δ166.3, 151.8, 138.1, 134.1, 129.5, 127.9, 123.1, 121.7, 119.2, 114.2, 113.9, 111.0, 102.8, 70.4, 66.4, 57.5, 40.8, 31.5, 29.9, 21.9, 14.0, 11.0; FAB HRMS calculated for [C$_{22}$H$_{27}$N$_5$O$_3$.H]410.2194, found 409.2187.

Y. 5-(4-Cyano-2-nitrophenylamino)-3-(N-methylpyrrolidin-2-ylmethyl)-1H-indole (R)-5-Amino-3-(N-methylpyrrolidin-2-ylmethyl)-1H-indole end 4-chloro-3-nitrobenzonitrile were used. Triethylamine was used as base, absolute ethanol was used as solvent, and the reaction was heated at reflux for 4 hours. Column chromatography afforded the title compound (80%) as a red solid: mp, 170°–171.0° C.; $^{13}$C NMR (CDCl$_3$) δ147.3, 137.1, 135.4, 132.0, 131.4, 128.6, 128.0, 125.3, 120.6, 117.9, 117.1, 116.3, 113.1, 111.9, 99.1, 68.1, 57.3, 40.6, 31.2, 28.1, 21.9, Anal. calcd for C$_{21}$H$_{21}$N$_5$O$_2$.0.05 CH$_2$Cl$_2$: C, 66.59; H, 5.60; N, 18.44. Found: C, 66.56; H, 5.26; N, 18.42.

Z. 3-(N-Methylpyrrolidin-2-ylmethyl)-5-(4-trifluoromethyl-2-nitrophenylamino)-1H-indole (R)-5-Amino-3-(N-methylpyrrolidin-2-ylmethyl)-1H-indole and 4-chloro-3-nitrobenzotrifluoride were used. Triethylamine was used as base, absolute ethanol was used as solvent, and the reaction was heated at reflux for 4.5 hours. Column chromatography afforded the title compound (38%) as a red foam: R$_f$=0.30 in 9:1:0.1 [methylene chloride/methanol/ammonium hydroxide]; $^{13}$C NMR (CDCl$_3$) δ147.0, 139.7, 135.1, 131.6, 131.0, 129.2, 128.5, 124.7, 124.2, 120.7, 118.6, 116.8, 116.6, 113.6, 112.6, 67.1, 57.4, 40.8, 31.3, 29.2, 21.9. FAB LRMS 419 [MH+]. Anal. calcd for C$_{21}$H$_{21}$N$_4$O$_2$.0.6 CH$_2$Cl$_2$: C, 55.27; H, 4.77; N, 11.94. Found: C, 55.44; H 4.58; N 11.52.

AA. 6-(5,6-Dichloro-2-nitrophenylamino)-3-(N-methylpyrrolidin-2-ylmethyl)-1H-indole (R)-5-Amino-3-(N-methylpyrrolidin-2-ylmethyl)-1H-indole and 1,2,3-trichloronitrobenzene were used. Sodium carbonate was used as base, N,N-dimethylformamide was used as solvent, and the reaction was heated at 125° C. for 3 hours. Column chromatography afforded the title compound (60%) as a red solid: R$_f$=0.4 in 9:1:0.1 [methylene chloride/methanol/ammonium hydroxide]; $^1$H NMR (CDCl$_3$) δ8.59 (br s, NH), 8.36 (br s, NH), 7.96 (d, J=9.1 Hz, 1H), 7.23 (d, J=8.6 Hz, 1H), 7.09 (s, 1H), 7.07 (d, J=9.1 Hz, 1H), 6.99 (d, J=1.9 Hz, 1H), 6.81 (dd, J=8.6 and 2.1 Hz, 1H), 3.15–3.05 (m, 2H), 2.54 (dd, J=13.8 and 9.6 Hz, 1H), 2.46–2.33 (m, 1H), 2.40 (s, 3H), 2.22 (dd, J=17.4 and 9.3 Hz, 1H), 1.84–1.48 (m, 4H); FAB HRMS calculated for [C$_{20}$H$_{20}$Cl$_2$N$_4$O$_2$.H]419.1044, found 419.1046.

BB. 5-(5-Chloro-2-nitrophenylamino)-3-(N-methylpyrrolidin-2-ylmethyl)-1H-indole (R)-5-Amino-3-(N-methylpyrrolidin-2-ylmethyl)-1H-indole and 2,4-dichloronitrobenzene were used. Sodium carbonate was used as base, N,N-dimethylformamide was used as solvent, and the reaction was heated at 125° C. for 3 hours. Column chromatography afforded the title compound (50%) as a red solid: FAB HRMS calculated for [C$_{20}$H$_{21}$ClN$_4$O$_2$.H]385.1434, found 385.1451.

CC. 5-(4-Cyano-2-nitrophenylamino)-3-[(2R,4R)-N-methyl-4-methoxypyrrolidin-2-ylmethyl]-1H-indole 5-Amino-3-[(2R, 4R)-N-methyl-4-methoxypyrrolidin-2-ylmethyl]-1H-indole and 4-chloro-3-nitrobenzonitrile were used. Triethylamine was used as base, absolute ethanol was used as solvent, and the reaction was heated at reflux for 3.5 hours. Column chromatography afforded the title compound (56%) as a red amorphous solid: $^1$H NMR (CDCl$_3$) δ9.92 (br s, NH), 8.54 (d, J=1.9 Hz, 1H), 8.52 (br s, NH), 7.45–7.39 (m, 3H 7.13 (br s, 1H), 7.03 (dd, J=8.8 and 1.7 Hz, 1H), 7.03 (d, J=8.9 Hz, 1H), 3.80–3.70 (m, 1H), 3.26 (s, 3H), 3.25–3.15 (m, 2H), 2.70 (dd, J=14.2 and 9.5 Hz, 1H), 2.49–2.38 (m, 1H), 2.42 (s, 3H), 2.25 (dd, J=10.8 and 5.3 Hz, 1H), 2.19–2.10 (m, 1H), 1.67–1.56 (m, 1H); $^{13}$C NMR (CDCl$_3$) δ147.2, 137.0, 135.1, 132.1, 131.3, 128.5, 128.0, 124.1, 120.3, 118.0, 117.0, 116.8, 114.0, 112.6, 99.0, 78.5, 65.9, 62.4, 56.5, 40.6, 39.2, 29.5; FAB HRMS calculated for [C$_{22}$H$_{23}$N$_5$O$_3$.H]406.1881, found 406.1872.

EXAMPLE 2

General Procedure for the Alkylation of (R)-5-(3-Nitropyrid-2-ylamino)-3-(pyrrolidin-2-ylmethyl)-1H-indoles To a stirred solution of (R)-5-(3-nitropyrid-2-ylamino)-3-(pyrrolidin-2-ylmethyl)-1H-indole (0.337 g, 1.00 mmol) and triethylamine (0.126 g, 1.25 mmol, 1.25 eq) in either anhydrous methylene chloride, anhydrous acetonitrile, absolute ethanol, or i-propanol (10 mL) at room temperature under nitrogen was added dropwise the alkylating agent (1.25 mmol). The resulting reaction solution was then stirred under nitrogen at room temperature or heated at reflux for 1–20 hours, depending on substrate. The resulting reaction mixture was directly column chromatographed using silica gel (approximately 25 g) and elution with methylene chloride: methanol: ammonium hydroxide [9:1:0.1] to afford the title compound.

Following this procedure the following compounds were prepared.

A. (R)-3-(N-Cyclopropylmethylpyrrolidin-2-ylmethyl)-5-(3-nitropyrid-2-ylamino)-1H-indole The reaction solvent was methylene chloride, the alkylating agent was bromomethyl cyclopropane, and the reaction solution was heated at reflux for 4 hours. Chromatography afforded the title compound (34%) as a dark red foam: $^{13}$C NMR (CDCl$_3$) δ155.7, 151.4, 133.5, 134.3, 129.4, 128.2, 123.1, 119.3, 114.4, 114.3, 113.0, 111.4, 65.0, 59.9, 55.0, 30.9, 30.3, 22.2, 10.0; FAB LRMS (m/z, relative intensity) 392 (MH$^+$,33), 374 (3), 307 (3), 267 (7), 220 (7), 154 (10), 124 (100); HRMS calculated for C$_{22}$H$_{25}$N$_5$O$_2$ 391.2011, found 391.1 988.

B. (R)-5-(3-Nitropyrid-2-ylamino)-3-(N-(2-propynyl)pyrrolidin-2-ylmethyl)-1H-indole The reaction solvent was methylene chloride, the alkylating agent was propargyl bromide, and the reaction solution was stirred at room temperature for 2 hours. Chromatography afforded the title compound (69%) as a dark red foam: $^{13}$C NMR (CDCl$_3$) δ155.7, 151.4, 135.5, 134.3, 129.4, 128,0, 123.1, 119.2, 114.3, 114.0, 113.0, 111.3, 79.1, 72.8, 61.6, 53.2, 40.8, 31.2, 29.8, 21.9; FAB LRMS (m/z, relative intensity) 376 (MH$^+$, 67), 350 (5), 307 (17), 267 (12), 220 (10), 136 (100); HRMS calculated for C$_{21}$H$_{21}$N$_5$O$_2$ 375.1697, found 375.1585.

C. (R)-5-(3-Nitropyrid-2-ylamino)-3-1N-(2-propenyl)pyrrolidin-2-ylmethyl)-1H-indole The reaction solvent was methylene chloride, the alkylating agent was allyl iodide, and the reaction solution was stirred at room temperature for 2.5 hours. Chromatography afforded the title compound (59%) as a dark red foam: $^{13}$C NMR (CDCl$_3$) δ155.7, 151.2, 135.6, 134.2, 129.9, 128.2, 126.9, 126.6, 125.6, 125.1, 119.6, 113.4, 112.2, 109.6, 67.4, 56.3, 53.7, 30.7, 27.2, 22.0; FAB LRMS (m/z, relative intensity) 378 (MH$^+$, 100), 336 (3), 267 (10), 220 (13), 136 (40). Anal. calcd. for C$_{21}$H$_{23}$N$_5$O$_2$.1.6 CHCl$_3$ [chloroform]: C, 47.75; H, 4.36, N, 12.32. Found: C, 47.98; H, 4.51; N, 12.56; HRMS calculated for C$_{21}$H$_{23}$N$_5$O$_2$377.1854, found 377.1881.

D. (R)-5-(3-Nitropyrid-2-ylamino)-3-(N-propylpyrrolidin-2-ylmethyl)-1H-indole

The reaction solvent was methylene chloride, the alkylating agent was propyl iodide, and the reaction solution was stirred at room temperature for 18 hours. Chromatography afforded the title compound (26%) as a dark red foam: $^{13}$C NMR (CDCl$_3$) δ155.6, 151.2, 135.5, 134.2, 130.0, 128.2, 126.8, 125.2, 119.7, 113.3, 113.1, 112.2, 109.6, 69.3, 56.9, 54.5, 30.6, 27.1, 22.0, 18.7, 11.4; FAB LRMS (m/z, relative intensity) 380 (MH$^+$, 80), 363 (3), 333 (5), 271 (6), 243 (8), 157 (60), 135 (43), 112 (100); EI LRMS (m/z, relative intensity) 379 (M$^+$, 0.2), 378 (1), 267 (3), 220 (5), 128 (14), 112 (100); HRMS calculated for C$_{21}$H$_{25}$N$_5$O$_2$ 379.2011, found 379.2027.

E. (R)-3-(N-Butylpyrrolidin-2-ylmethyl)-5-(3-nitropyrid-2-ylamino)-1H-indole

The reaction solvent was methylene chloride, the alkylating agent was butyl iodide, and the reaction solution was stirred at room temperature for 18 hours. Chromatography afforded the title compound (33%) as a dark red foam: $^{13}$C NMR (CDCl$_3$) δ155.7, 151.2, 135.5, 134.2, 130.0, 128.2, 126.8, 125.2, 119.7, 113.3, 113.2, 112.2, 109.5, 69.2, 55.0, 54.5, 30.6, 27.1, 26.8, 22.0, 20.0, 13.3; LRMS (m/z, relative intensity) 393 (M$^+$, 0.2), 392 (1), 391 (1), 267 (2), 220 (3), 126 (100); HRMS calculated for C$_{21}$H$_{27}$N$_5$O$_2$ 393.2167, found 393.2156.

F. 3-(N-(2-Hydroxycyclopentyl)pyrrolidin-2-ylmethyl)-5-(3-nitropyrid-2-yl-amino)-1H-indole The reaction solvent was methylene chloride, the alkylating agent was cyclopentene oxide, and the reaction solution was heated at reflux (82° C.) for 20 hours. Chromatography afforded the title compound (57%) as a dark red foam comprising a mixture of diastereomers at the carbon adjacent to the alcohol: $^{13}$C NMR (CDCl$_3$) δ155.6, 151.3, 135.5, 134.2, 129.3, 129.3, 128.1, 123.3, 123.2, 119.0, 118.9, 114.6, 114.2, 114.2, 113.0, 111.4, 111.4, 75.5, 74.7, 70.6, 69.1,62.4, 61.7, 51.1,48.2, 34.6, 32.8, 31.1, 30.9, 30.8, 30.3, 29.2, 23.1, 23.0, 22.7, 21.7, 20.5; LRMS (m/z, relative intensity) 421 (M$^+$, 0.2), 420 (1), 419 (1), 418 (55), 380 (13), 348 (22), 279 (100), 218 (30), 169 (44), 154 (91); HRMS calculated for C$_{23}$H$_{27}$N$_5$O$_3$ 421.2116, found 421.2040.

G. (R)-3-(N-Ethylpyrrolidin-2-ylmethyl)-5-(3-nitropyrid-2-ylamino-1H-indole

The reaction solvent was acetonitrile, the alkylating agent was ethyl iodide, and the reaction solution was stirred at room temperature for 7 hours. Chromatography afforded the title compound (32%) as a dark red foam: $^{13}$C NMR (CDCl$_3$) δ155.6, 151.2, 135.5, 134.2, 130.0, 128.2, 126.8, 125.2, 119.7, 113.3, 113.2, 112.2, 109.5, 68.8, 53.8, 50.1, 50.7, 27.2, 21.9, 10.5; FAB LRMS (m/z, relative Intensity) 366 (MH$^+$, 100), 332 (8), 257 (8), 229 (15), 157 (55), 135 (37); HRMS calculated for C$_{20}$H$_{23}$N$_5$O$_2$ 365.1854, found 365.1836.

H. (R)-5-(3-Nitropyrid-2-ylamino)-3-(N-pentylpyrrolidin-2-ylmethyl)-1H-indole

The reaction solvent was methylene chloride, the alkylating agent was pentyl iodide, and the reaction solution was stirred at room temperature for 18 hours. Chromatography afforded the title compound (23%) as a dark red foam: $^{13}$C NMR (CDCl$_3$) δ155.6, 151.2, 135.5, 134.2, 130.0, 128.2, 126.8, 125.3, 119.7, 113.3, 113.1, 112.2, 109.6, 69.1, 55.2, 54.5, 30.7, 28.7, 27.2, 24.5, 22.0, 21.8, 13.7; FAB LRMS (m/z, relative intensity) 408 (MH$^+$, 36), 327 (8), 136 (100); HRMS calculated for C$_{23}$H$_{29}$N$_5$O$_2$ 407.2324, found 407.2299.

I. (R)-3-(N-(2-Methoxyethyl)pyrrolidin-2-ylmethyl)-5-(3-nitropyrid-2-ylamino)-1H-indole The reaction solvent was acetonitrile/methylene chloride (1:1), the alkylating agent was 2-bromoethyl methyl ether with sodium iodide (1.25 mmol), and the reaction solution was heated at reflux (40° C.) for 7 hours. Chromatography afforded the title compound (32%) as a dark red foam: $^{13}$C NMR (CDCl$_3$) δ155.7, 151.2, 135.5, 134.2, 129.8, 128.1, 126.9, 125.0, 119.6, 113.4, 113.3, 112.2, 109.4, 69.1, 66.9, 59.0, 55.4, 46.4, 29.9, 26.8, 22.0; LRMS (m/z, relative intensity) 395 (M$^+$, 0.5), 394 (1), 348 (20), 267 (39), 220 (68), 128 (100); HRMS calculated for C$_{21}$H$_{25}$N$_5$O$_3$ 395.1960, found 395.1940.

J. (R)-3-(N-(2-Cyanoethyl)pyrrolidin-2-ylmethyl)-5-(3-nitropyrid-2-ylamino)-1H-indole The reaction solvent was absolute ethanol, the alkylating agent was acrylonitrile, no base was used, and the reaction solution was stirred at room temperature for 18 hours. Chromatography afforded the title compound (27%) as a dark red foam: $^1$H NMR (CDCl$_3$) δ10.1 (br s, 1H), 8.52 (dd, J=8.4 and 1.6 Hz, 1H), 8.44 (dd, J=1.5 and 4.4 Hz, 1H), 8.19 (br s, 1H), 7.76 (br s, 1H), 7.38–7.27 (m, 2H), 7.09 (d, J=1.5 Hz, 1H), 6.76 (dd, J=4.5 and 8.3 Hz, 1H), 3.27–3.13 (m, 2H), 3.08–3.01 (m, 1H), 2.88–2.78 (m, 1H), 2.74–2.49 (m, 4H), 2.32–2.22 (m, 1H), 1.90–1.57 (m, 4H); LRMS (m/z, relative intensity) 390 (M$^+$, 17), 335 (5), 268 (54), 220 (24), 123 (100); HRMS calculated for C$_{21}$H$_{22}$N$_6$O$_2$ 390.1807, found 390.1773.

K. (R)-3-(N-2-Cyanomethyl)pyrrolidin-2-ylmethyl)-5-(3-nitropyrid-2-ylamino)-1H-indole The reaction solvent was acetonitrile/methylene chloride (3:2), the alkylating agent was bromoacetonitrile, and the reaction solution was stirred at room temperature for 18 hours. Chromatography afforded the title compound (76%) as a dark red foam: $^{13}$C NMR (CDCl$_3$) δ155.8, 151.4, 135.5, 134.2, 129.6, 128.1, 127.9, 123.3, 119.3, 115.5, 114.1, 113.1, 111.5, 62.1, 53.7, 40.7, 31.2, 29.9, 22.2; LRMS (m/z, relative intensity) 376 (M$^+$, 6), 375 (28), 279 (58), 180 (10), 169 (14), 109 (100); HRMS calculated for C$_{20}$H$_{20}$N$_6$O$_2$ 376.1650, found 376.1641.

EXAMPLE 3

General Procedure for the Formation of 5-Arylamino-3-(piperid-4-yl)-1H-indoles, 5-Arylamino-3-(1,2,5,6-tetrahydropyrid-4-yl)-1H-indoles, or 5-Aryloxy-3-(1,2,5,6-tetrahydropyrid-4-yl)-1H-indoles from the Deprotection of 5-Arylamino-3-(N-t-butoxycarbonylpiperid-4-yl)-1H-indoles, 5-Arylamino-3-(N-t-butoxycarbonyl-1,2,5,6-tetrahydropyrid-4-yl)-1H-indoles, or 5-Aryloxy-3-(N-t-butoxycarbonyl-1,2,5,6-tetrahydropyrid-4-yl)-1H-indoles, Respectively HCl gas was passed through a stirred solution of 5-arylamino-3-(N-t-butoxycarbonylpiperid-4-yl)-1H-indole, 5-arylamino-3-(N-t-butoxycarbonyl-1,2,5,6-tetrahydropyrid-4-yl)-1H-indole, or 5-aryloxy-3-(N-t-butoxycarbonyl-1,2,5,6-tetrahydropyrid-4-yl)-1H-indole (2.00 mmol) in absolute methanol (20 mL), at 0° C. for approximately 15 minutes. The resulting mixture was stirred at 0° C. under nitrogen for 6 hours. The mixture was then filtered to afford the 5-arylamino-3-(piperid-4-yl)-1H-indole 5-arylamino-3-(1,2,5,6-tetrahydropyrid-4-yl)-1H-indole, or 5-aryloxy-3-(1,2,5,6-tetrahydropyrid-4-yl)-1H-indole as a HCl salt.

A. 5-(3-Nitropyrid-2-ylamino)-3-(piperid-4-yl)-1H-indole 3-(N-t-Butoxycarbonylpiperid-4-yl)-5-(3-nitropyrid-2-ylamino)-1H-indole was used. Filtration afforded the title compound (83%) as a dark red solid: mp, decomposes 220° C.; $^{13}$C NMR (DMSO-d$_6$) δ155.5, 150.8, 135.7, 134.4, 129.2, 127.9, 126.0, 121.8, 119.3, 118.3, 114.5, 113.4, 111.5, 43.5, 31.0, 29.0. LRMS (m/z, relative Intensity) 337 (M$^+$, 31), 302 (44), 281 (31), 240 (100). Anal. calcd. for C$_{18}$H$_{19}$N$_5$O$_2$. 3.0 HCl: C, 48.39; H, 4.96; N, 15.68. Found: C, 43.73; H, 5.16; N, 15.21.

B. 5-(3-Nitropyrid-2-ylamino)-3-(1,2,5,6-tetrahydropyrid-4-yl)-1H-indole 3-(N-t-Butoxycarbonyl-1,2,5,6-tetrahydropyrid-4-yl)-5-(3-nitropyrid-2-ylamino)-1H-indole was used. Filtration afforded the title compound (85%) as a dark red solid: mp, decomposes 204° C.; $^{13}$C NMR (DMSO-d$_6$) δ155.3, 150.7, 135.7, 134.9, 130.5, 130.0, 128.1, 124.7, 124.3, 119.6, 115.7, 114.7, 113.5, 111.8, 43.6, 41.2, 23.9. Anal. calcd. for C$_{18}$H$_{19}$N$_5$O$_2$.2.75 HCl.CH$_3$OH [methanol]: C, 48.80; H, 5.12; N, 14.98. Found: C, 49.11; H, 5.14; N, 15.34.

C. 5-(5-Nitropyrid-2-ylamino)-3-(1,2,5,6-tetrahydropyrid-4-yl)-1H-indole 3-(N-t-Butoxycarbonyl-1,2,5,6-tetrahydropyrid-4-yl)-5-(5-nitropyrid-2-ylamino)-1H-indole was used. Filtration afforded the title compound (87%) as a dark red solid: mp, decomposes 273° C.; $^{13}$C NMR (DMSO-d$_6$) δ159.9, 146.7, 135.2, 134.2, 132.2, 131.9, 130.1, 124.5, 124.4, 118.0, 115.0, 113.0, 112.1, 41.9, 40.6, 24.7; LRMS (m/z, relative intensity) 336 (20), 355 (M$^+$, 100), 306 (50), 294 (53), 167 (67). Anal. calcd. for C$_{18}$H$_{17}$N$_5$O$_2$.2.1 HCl: C, 52.48; H, 4.67; N, 17.00. Found: C, 52.41; H, 4.54; N, 16.71.

D. 5-(3-Nitropyrid-2-yloxy)-3-(1,2,5,6-tetrahydropyrid-4-yl)-1H-indole 3-(N-t-Butoxycarbonyl-1,2,5,6-tetrahydropyrid-4-yl)-5-(3-nitropyrid-2-yloxy)-1H-indole was used. Filtration afforded the title compound (53%) as a yellow solid: mp, 244.0°–245.0° C.; $^{13}$C NMR (DMSO-d$_6$) δ155.9, 152.1, 146.2, 135.9, 134.8, 134.1, 129.7, 125.3, 124.6, 118.7, 116.2, 114.9, 112.7, 112.4, 112.3, 41.2, 24.0. Anal. calcd. for C$_{18}$H$_{16}$N$_4$O$_3$.1.5 HCl.0.5 CH$_3$OH [methanol]: C, 54.59; H, 4.83; N, 13.76. Found: C, 54.21; H, 4.56; N, 13.44.

E. 5-(5-Nitropyrid-2-yloxyl)-3-(1,2,5,6-tetrahydropyrid-4-yl)-1H-indole 3-(N-t-Butoxycarbonyl-1,2,5,6-tetrahydropyrid-4-yl)-5-(5-nitropyrid-2-yloxy)-1H-indole was used. Filtration afforded the title compound (19%) as an orange foam: $^{13}$C NMR (DMSO-d$_6$) δ167.7, 146.2, 144.9, 140.0, 135.5, 134.8, 129.7, 124.2, 115.5, 112.7, 112.3, 110.9, 44.7, 42.8, 28.1; LRMS (m/z, relative intensity) 336 (M$^+$, 24), 307 (9), 210 (100), 185 (40); HRMS calculated for C$_{18}$H$_{16}$N$_4$O$_3$ 336.1224, found 336.1196.

EXAMPLE 4

3-(2-Dimethylaminoethyl)-5-(3-aminopyrid-2-ylamino)-1H-indole

A mixture of 3-(2-dimethylaminoethyl)-5-(3-nitropyrid-2-ylamino)-1H-indole (1.27 g, 3.90 mmol), 10% Pd on carbon (200 mg), and absolute ethanol (20 mL) was shaken under a hydrogen atmosphere (3 atm) for 2 hours. The reaction mixture was filtered through diatomaceous earth, and the filtrate was evaporated under reduced pressure. The residue was column chromatographed using silica gel (approximately 40 g) and elution with absolute methanol to afford the title compound (0.74 g, 64%) as an off-white solid: mp., 196.0°–198.0° C. with effervescence; $^{13}$C NMR (DMSO-d$_6$) δ145.3, 134.5, 133.6, 132.1, 131.0, 127.3, 122.6, 118.8, 116.1, 114.2, 112.1, 110.8, 108.6, 60.1, 45.2, 23.4; HRMS calculated for C$_{17}$H$_{21}$N$_5$ 295.1793, found 295.1810. Anal. calcd. for C$_{17}$H$_{21}$N$_5$.0.4 C$_2$H$_6$O [ethanol]: C, 68.13; H, 7.52; N, 22.32. Found: C, 68.12; H, 7.19; N, 22.51.

EXAMPLE 5

3-(2-Dimethylaminoethyl)-5-(3-phenylcarbonylaminopyrid-2-ylamino)-1H-indole

To a stirred solution of 3-(2-dimethylaminoethyl)-5-(3-aminopyrid-2-ylamino)-1H-indole (0.157 g, 0.53 mmol) and triethylamine (74 µL, 0.54 mmol, 1.0 eq) in anhydrous tetrahydrofuran (3 mL) was added dropwise benzoyl chloride (62 µL, 0.54 mmol, 1.0 eq). The resulting reaction mixture was stirred at room temperature under nitrogen for 15 minutes. A saturated solution of sodium hydrogen carbonate (10 mL) was added, and this aqueous mixture was extracted with ethyl acetate (3×10 mL). The organic extracts were combined, dried (MgSO$_4$), and evaporated under reduced pressure. The residue was triturated in diethyl ether to afford the title compound (0.082 g, 39%) as an amorphous solid: $^{13}$C NMR (DMSO-d$_6$) δ166.5, 151.9, 144.5, 134.5; 132.7, 132.5, 131.6, 128.3, 128.0, 127.2, 122.8, 119.6, 117.3, 113.3, 112.1, 110.8, 110.4, 59.9, 45.0, 23.1; LRMS (m/z, relative intensity) 399 (M$^+$, 100), 354 (33), 249 (10), 235 (18), 204 (40), 160 (86); HRMS calculated for C$_{24}$H$_{25}$N$_5$O 399.2062, found 399.2080.

EXAMPLE 6

3-(2-Dimethylaminoethyl)-5-(6-benzylaminocarbonyl-3-methylthio-1,2,4-triazin-5-ylamino)-1H-indole To a stirred mixture of 3-(2-dimethylaminoethyl)-5-(6-ethoxycarbonyl-3-methylthio-1,2,4-triazin-5-ylamino)-1H-indole (0.25 g, 0.62 mmol) in methylene chloride (5 mL) at room temperature under nitrogen was added dropwise benzylamine (0.14 mL, 1.25 mmol, 2.0 eq). The resulting reaction mixture was stirred at room temperature under nitrogen for 48 hours, and then filtered. The resulting yellow solid was recrystallized from methanol: ethyl acetate (4:1) to afford the title compound (0.063 g, 22%) as a yellow solid: mp, 207.0°–209.0° C.; FAB HRMS calculated for [C$_{24}$H$_{27}$N$_7$OS.H$^+$]482.2079, found 462.2054. Anal. calcd. for C$_{24}$H$_{27}$N$_7$OS.3/4 H$_2$O: C, 60.67; H, 6.05; N, 20.63. Found: C, 60.58; H, 5.73; N, 20.58.

EXAMPLE 7

N-Methyl-3-(5-phenylcarbonylaminoindol-3-yl)succinamide

A solution of 5-phenylcarbonylamino-1H-indole (2.50 g, 10.58 mmol) [Chem. Abstracts, 10991 g (1954)] and N-methylmaleimide (2.94 g, 26.46 mmol, 2.5 eq) in glacial acetic acid (75 mL) was heated at reflux under nitrogen for 24 hours. The resulting reaction solution was evaporated under reduced pressure, and the residual oil was dissolved in ethyl acetate (50 mL). This solution was washed with a saturated solution of sodium hydrogen carbonate (2×25 mL), dried (MgSO$_4$), and evaporated under reduced pressure. The residual oil was column chromatographed using silica gel (approximately 100 g) and elution with ethyl acetate: hexanes [gradient 1:3 to 1:1] to afford the title compound (1.06 g, 29%) as a white solid: mp, 226.5°–227.5° C.; FAB LRMS (m/z, relative intensity) 348 (MH$^+$, 100), 332 (2), 275 (4), 263 (5). Anal. calcd. for C$_{20}$H$_{17}$N$_3$O$_3$.1/8 H$_2$O: C, 68.71; H, 4.97; N, 12.02. Found: C, 68.68; H, 4.74; N, 11.91.

EXAMPLE 8

5-Benzylamino-3-(N-methylpyrrolidin-3-yl)-1H-indole

To a stirred solution of N-methyl-3-(5-phenylcarbonylaminoindol-3-yl)succinamide (18.31 g, 52.71 mmol) in anhydrous tetrahydrofuran (270 mL) at 0° C. was added lithium aluminum hydride (20.01 g, 527 mmol, 10 eq) as a solid portionwise over 45 minutes. The resulting reaction mixture was stirred at room temperature under nitrogen for 24 hours. Sodium sulfate decahydrate (50 g) was then carefully added to the reaction mixture followed by water (5 mL) and ethyl acetate (100 mL). The resulting mixture was stirred at room temperature for 1 hour. The reaction mixture was filtered, and the filtrate was evaporated under reduced pressure. The residual oil was column chromatographed using silica gel (approximately 500 g) and elution with ethyl acetate: methanol: triethylamine [gradient 9:0:1 to 8:1:1] to afford the title compound (7.90 g, 49%) as a pale yellow oil: $^{13}$C NMR (acetone-d$_6$) δ142.9, 142.1, 132.3, 129.3, 128.6, 127.5, 121.9, 118.6, 112.8, 112.5, 102.0, 63.6, 57.1, 49.9, 42.8, 36.5, 33.0; FAB LRMS (m/z, relative intensity) 306 (MH$^+$, 100), 263 (4), 248 (4), 223 (8).

EXAMPLE 9

5-Amino-3-(N-methylpyrrolidin-3-yl)-1H-indole

A mixture of 5-benzylamino-3-(N-methylpyrrolidin-3-yl)-1H-indole (7.80 g, 25.5 mmol), ammonium formate (16.10 g, 255 mmol, 10 eq), and 10% Pd on carbon (0.78 g) in absolute ethanol (250 mL) was heated at reflux under nitrogen for 1 hour. The reaction was filtered, and filtrate evaporated under reduced pressure. The residual oil was column chromatographed using silica gel (approximately 200 g) and elution with 0.3% triethylamine in methanol to afford the title compound (0.90 g, 16%) as a pale yellow oil: $^1$H NMR (CD$_3$OD) δ7.13 (d, J=8.5 Hz, 1H), 6.94 (br s, 2H), 6.65 (dd, J=2.0 and 8.5 Hz, 1H), 4.91 (s, 2-NH), 3.66–3.50 (m, 1H), 3.17–3.08 (br t, 1H), 2.96–2.85 (m, 1H), 2.67–2.50 (m, 2H), 2.40 (s, 3H), 2.37–2.24 (m, 1H), 2.08–1.93 (m, 1H); FAB LRMS (m/z, relative intensity) 216 (MH$^+$, 100).

EXAMPLE 10

(R)-3-(N-Benzyloxycarbonylpyrrolidin-2-ylcarbonyl)-5-dibenzylamino-1H-indole

To a stirred mixture of (R)-N-carbobenzyloxyproline (3.59 g, 14.41 mmol) and N,N-dimethylformamide (0.1 mL) in methylene chloride (45 mL) was added dropwise oxalyl chloride (1.87 mL, 21.62 mmol, 1.5 eq). The resulting effervescing mixture was stirred at room temperature under nitrogen for 1.5 hours. The reaction solution was then evaporated under reduced pressure, yielding the residue [(R)-N-carbobenzyloxyproline acid chloride] which was dissolved in anhydrous ether (50 mL). This solution was added dropwise to a stirred, preformed solution of 5-dibenzylaminoindole (9.00 g, 28.81 mmol, 2.0 eq) and ethyl magnesium bromide (3.0M in ether, 10.08 mL, 30.25 mmol, 2.1 eq) in anhydrous ether (75 mL), which had been stirring at room temperature under nitrogen for 30 minutes prior to the addition of the ethereal solution of the (R)-N-carbobenzyloxyproline acid chloride. The resulting reaction mixture was stirred at room temperature under nitrogen for 30 minutes, and then ethyl acetate (100 mL) and a saturated solution of sodium hydrogen carbonate (75 mL) were added. The organic layer was removed, and the aqueous layer was extracted with ethyl acetate (100 mL). The organic extracts were combined, dried (MgSO$_4$), and evaporated under reduced pressure to afford a green oil. Trituration of this oil in anhydrous ether (50 mL) afforded the title compound as a white solid: mp, 176.0°–177.0° C.; LRMS (m/z, relative intensity) 543 (100, M$^+$), 453 (10), 407 (7), 339 (40), 307 (10), 247 (10), 154 (38); [α]$^{25}$=+112° (THF, c=1.0); Anal. calcd. for C$_{35}$H$_{33}$N$_3$O$_3$: C, 77.32; H, 6.12; N, 7.73. Found: C, 77.35; H, 6.30; N, 7.66.

EXAMPLE 11

(R)-5-Dibenzylamino-3-(N-methylpyrrolidin-2-ylmethyl)-1H-indole

To a stirred mixture of lithium aluminum hydride (0.96 g, 25.2 mmol, 2.0 eq) in anhydrous tetrahydrofuran (125 mL) at 0° C. was added dropwise a solution of (R)-3-(N-benzyloxycarbonylpyrrolidin-2-ylcarbonyl)-5-dibenzylamino-1H-indole (6.90 g, 12.69 mmol) in anhydrous tetrahydrofuran (25 mL). The resulting reaction mixture was stirred at room temperature under nitrogen for 30 minutes. Lithium borohydride (0.55 g, 25.2 mmol, 2.0 eq) was then added, and the reaction mixture was heated at reflux (66° C.) under nitrogen for 6 hours. The reaction mixture was cooled, and water (1.5 mL), a solution of sodium hydroxide (20%, 1.5 mL), and more water (4.5 mL) were added, sequentially. The resulting mixture was stirred at room temperature under nitrogen for 1 hour, filtered through diatomaceous earth, and the filtrate was evaporated under reduced pressure to yield a green oil (8.8 g). This oil was dissolved in absolute ethanol (90 mL), and cesium carbonate (8.0 g) and sodium carbonate (8.0 g) were added. The resulting mixture was heated at reflux for 12 hours. The reaction mixture was then evaporated under reduced pressure, and the residue was partitioned between a saturated solution of sodium hydrogen carbonate (50 mL) and ethyl acetate (100 mL). The organic layer was removed, and the aqueous layer was extracted with ethyl acetate (100 mL). The organic extracts were combined, dried ($MgSO_4$), and evaporated under reduced pressure to afford a brown oil. Column chromatography of this oil using silica gel (approximately 200 g) and elution with methylene chloride/methanol/ammonium hydroxide [9:1:0.1] afforded the title compound (4.63 g, 89%) as a pale green foam: $^1H$ NMR ($CDCl_3$) δ7.82 (br s, NH), 7.35–7.19 (m, 10H), 7.20 (d, J=8.6 Hz, 1H), 6.95 (d, J=2.1 Hz, 1H), 6.85 (dd, J=2.3 and 8.7 Hz, 1H), 6.80 (d, J=2.2 Hz, 1H), 4.65 (s, 4H), 3.25–3.02 (m, 2H), 2.52 (dd, J=9.5 and 13.9 Hz, 1H), 2.39–2.15 (m, 2H), 2.30 (s, 3H), 1.85–1.40 (m, 4H); $^{13}C$ NMR ($CDCl_3$) δ143.2, 139.7, 130.5, 128.5, 128.2, 127.3, 126.8, 122.9, 112.5, 112.2, 111.8, 103.4, 67.0, 57.4, 56.4, 40.6, 31.4, 29.7, 21.9; HRMS calculated for $C_{28}H_{31}N_3$ 409.2520, found 409.2475.

EXAMPLE 12

(R)-5-Amino-3-(N-methylpyrrolidin-2-ylmethyl)-1H-indole

A mixture of (R)-5-dibenzylamino-3-(N-methylpyrrolidin-2-ylmethyl)-1H-indole (1.08 g, 2.64 mmol) and palladium [II] hydroxide on carbon (0.6 g) in absolute ethanol (25 mL) was shaken under a hydrogen atmosphere (3 atm) at 40° C. for 4 hours. The resulting mixture was filtered through diatomaceous earth, and the filtrate was evaporated under reduced pressure to afford the title compound (0.60 g, 2.62 mmol, 99%) as a white foam: $^1H$ NMR (DMSO-$d_6$) δ10.65 (br s, NH), 7.14 (d, J=2.2 Hz, 1H), 7.12 (d, J=8.6 Hz, 1H), 6.85 (d, J=1.6 Hz, 1H), 6.60 (dd, J=2.0 and 8.6 Hz, 1H), 3.63–2.83 (m, 7H), 2.78 (s, 3H), 2.05–1.67 (m, 4H); $[\alpha]^{25}$=+9° (MeOH, c=1.0); HRMS calculated for $C_{14}H_{19}N_3$: 229.1575; found: 229.1593.

EXAMPLE 13

(R)-3-(N-Benzyloxycarbonylpyrrolidin-2-ylmethyl)-5-dibenzylamino-1H-indole

To a stirred solution of (R)-3-(N-benzyloxycarbonylpyrrolidin-2-ylcarbonyl)-5-dibenzylamino-1H-indole (1.50 g, 2.75 mmol) in anhydrous tetrahydrofuran (30 mL) was added lithium borohydride (0.24 g, 11.0 mmol, 4.0 eq) as a solid. The resulting reaction mixture was heated at reflux for 4 hours. A saturated solution of sodium hydrogen carbonate (10 mL) was then added, and this mixture was stirred at room temperature for 30 minutes. This aqueous mixture was then extracted with ethyl acetate (3×25 mL), and the organic extracts were combined, dried ($MgSO_4$), and evaporated under reduced pressure. Column chromatography of the residue using silica gel (approximately 50 g) and elution with ethyl acetate/hexanes [1:3] afforded the title compound (1.02 g, 70%) as a white foam: FAB LRMS (m/z, relative intensity) 530 ($MH^+$, 87), 529 ($M^+$, 100), 439 (10), 409 (10), 325 (32), 235 (20).

EXAMPLE 14

(R)-5-Amino-3-(pyrrolidin-2-ylmethyl)-1H-indole

A mixture of (R)-3-(N-benzyloxycarbonylpyrrolidin-2-ylmethyl)-5-dibenzylamino-1H-indole (7.90 g, 14.91 mmol) and moist palladium (ll) hydroxide on carbon (Peariman's catalyst, 3.16 g) in absolute ethanol (100 mL) was shaken under a hydrogen atmosphere (3 arm) for 12 hours at room temperature. The resulting mixture was filtered through diatomaceous earth, and the filtrate was evaporated and dried under reduced pressure to afford the title compound as a white foam (3.20 g, 100%): $^1H$ NMR ($CD_3OD$) δ7.18 (d, J=8.5 Hz, 1H), 7.08 (s, 1H), 6.92 (d, J=2.0 Hz, 1H), 6.69 (dd, J=1.9 and 8.5 Hz, 1H),3.81–3.69(m, 1H),3.30–2.95(m,4H), 2.09–1.55(m, 4H); $^{13}C$ NMR ($CD_3OD$) δ140.1, 133.4, 129.1, 125.0, 114.6, 113.1, 109.8, 105.1, 62.1, 46.0, 31.1, 29.1, 24.3; LRMS (m/z, relative intensity) 215 ($M^+$, 2), 198 (1), 146 (100), 128 (7), 117 (9), 70 (60).

EXAMPLE 15

General Procedure for the Condensation of 5-Amino-3-(N-t-butoxycarbonyl-1,2,5,6-tetrahydropyrid-4-yl)-1H-indole, 5-Amino-3-(N-t-butoxycarbonylpiperid-4-yl)-1H-indole, or 3-(N-t-Butoxycarbonyl-1,2,5,6-tetrahydropyrid-4-yl)-5-hydroxy-1H-indole with 2-Chloropyridines to Form 3-(N-t-Butoxycarbonyl-1,2,5,6-tetrahydropyrid-4-yl)-5-(pyrid-2-ylamino)-1H-indoles, 3-(N-t-Butoxycarbonylpiperid-4-yl)-5-(pyrid-2-ylamino)-1H-indoles or 3-(N-t-Butoxycarbonyl-1,2,5,6-tetrahydropyrid-4-yl)-5-(pyridin-2-yloxy)-1H-indoles, respectively To a solution of 5-amino-3-(N-t-butoxycarbonyl-1,2,5,6-tetrahydropyrid-4-yl)-1H-indole, 5-amino-3-(N-t-butoxycarbonylpiperid-4-yl)-1H-indole, or 3-(N-t-butoxycarbonyl-1,2,5,6-tetrahydropyrid-4-yl)-5-hydroxy-1H-indole (10.0 mmol) and a base (12.0 mmol, 1.2 eq) in anhydrous tetrahydrofuran or dioxane (35 mL) was added the 2-chloropyridine (11.0 mmol, 1.1 eq). The resulting reaction solution was stirred at reflux or at room temperature under nitrogen for 3–48 hours, depending on substrate and reaction solvent. A saturated solution of sodium hydrogen carbonate (25 mL) was then added to the reaction mixture, and this aqueous mixture was extracted with ethyl acetate (3×25 mL). The organic extracts were combined, dried (Mg $SO_4$), and evaporated under reduced pressure. The extraction residue was column chromatographed using silica gel (approximately 150 g) and elution with the appropriate solvent system to afford the desired 3-(N-t-butoxycarbonyl-1,2,5,6-tetrahydropyrid-4-yl)- 5-(pyrid-2-ylamino)-1H-indole, 3-(N-t-butoxycarbonylpiperid-4-yl)-5-(pyrid-2-ylamino)-1H-indole or 3-(N-t-butoxycarbonyl-1,2,5,6-tetrahydropyrid-4-yl)-5-(pyridin-2-yloxy)-1H-indole.

Following this procedure the following compounds were prepared.

A. 3-(N-t-Butoxycarbonyl-1,2,5,6-tetrahydropyrid-4-yl)-5-(3-nitropyrid-2-ylamino)-1H-indole 5-Amino-3-(N-t-butoxycarbonyl-1,2,5,6-tetrahydropyrid-4-yl)-1H-indole and 2-chloro-3-nitropyridine were used. Triethylamine was the base, tetrahydrofuran was the reaction solvent, the reaction time was heated at reflux (66° C.) for 8 hours, and the chromatographic solvent system was diethyl ether/hexanes [gradient 1:1 to 1:0] to afford the title compound (73%) as a dark red foam: $^1$H NMR (CDCl$_3$) δ10.1 (br s, 1H), 8.51 (dd, J=1.8 and 8.4 Hz, 1H), 8.43 (dd, J=1.8 and 4.5 Hz, 1H), 8.20 (br s, 1H), 8.00 (br s, 1H), 7.40–7.35 (m, 2H), 7.19 (d, J=2.5 Hz, 1H), 6.75 (dd, J=4.5 and 8.3 Hz, 1H), 6.12 (br m, 1H), 4.12 (br m, 2H), 3.66 (br t, J=5.7 Hz, 2H), 2.55 (br m, 2H), 1.49 (s, 9H); TLC [diethyl ether]: R$_f$=0.4.

B. 3-(N-t-Butoxycarbonyl-1,2,5,6-tetrahydropyrid-4-yl)-5-(5-nitropyrid-2-ylamino)-1H-indole 5-Amino-3-(N-t-butoxycarbonyl-1,2,5,6-tetrahydropyrid-4-yl)-1H-indole and 2-chloro-5-nitropyridine were used. Triethylamine was the base, tetrahydrofuran was the reaction solvent, the reaction was heated at reflux (66° C.) for 48 hours, and the chromatographic solvent system was methylene chloride/hexanes [1:1] to afford the title compound (76%) as a red foam: $^1$H NMR (CD$_3$OD) δ8.95 (d, J=2.4 Hz, 1H), 8.18 (dd, J=2.8 and 9.3 Hz, 1H), 7.96 (br s, 1H), 7.38 (d, J=8.9 Hz, 1H), 7.32 (s, 1H), 7.24 (dd, J=2.2 and 8.8 Hz, 1H), 6.70 (d, J=9.0 Hz, 1H), 6.10 (br m, 1H), 4.89 (s, 2-NH 4.08 (br m, 2H), 3.65 (br t, J=5.6 Hz, 2H), 2.56 (br m, 2H), 1.49 (s, 9H); TLC [diethyl ether]: R$_f$=0.45.

C. 3-(N-t-Butoxycarbonylpiperid-4-yl)-5-(3-nitropyrid-2-ylamino)-1H-indole

5-Amino-3-(N-t-butoxycarbonylpiperid-4-yl)-1H-indole and 2-chloro-3-nitropyridine were used. Triethylamine was the base, dioxane was the reaction solvent, the reaction was heated at reflux (101° C.) for 5 hours, and the chromatographic solvent system was ethyl acetate [30–40%] in hexanes to afford the title compound (70%) as a dark red foam: $^1$H NMR (CDCl$_3$) δ155.8, 155.0, 151.6, 135.5, 134.6, 129.4, 126.9, 121.3, 120.8, 119.8, 114.8, 113.1, 111.5, 79.4, 44.5, 33.6, 32.8, 28.5. Anal. calcd. for C$_{23}$H$_{27}$N$_5$O$_4$·1/4 C$_4$H$_8$O$_2$ [ethyl acetate]: C, 62.73; H, 6.36; N, 15.24. Found: C, 62.51; H, 6.08; N, 15.21.

D. 3-(N-t-Butoxycarbonyl-1,2,5,6-tetrahydropyrid-4-yl)-5-(3-nitropyrid-2-yloxy)-1H-indole 3-(N-t-Butoxycarbonyl-1,2,5,6-tetrahydropyrid-4-yl)-5-hydroxy-1H-indole and 2-chloro-3-nitropyridine were used. Sodium hydride (60% in oil) was the base, tetrahydrofuran was the reaction solvent, the reaction was stirred at room temperature for 3 hours, and the chromatographic solvent system was diethyl ether/hexanes [gradient 1:1 to 4:1] to afford the title compound (62%) as a yellow solid: top, 206.0°–208.0° C. with effervescence; $^1$H NMR (DMSO-d$_6$) δ8.53 (dd, J=1.8 and 8.3 Hz, 1H), 8.33 (dd, J=1.8 and 4.4 Hz, 1H), 7.62 (d, J=2.0 Hz, 1H), 7.50 (br s, 1H), 7.42 (d, J=8.6 Hz, 1H), 7.30 (dd, J=4.4 and 8.3 Hz, 1H), 6.94 (dd, J=2.0 and 8.6 Hz, 1H), 6.05–6.01 (m, 1H), 4.02–3.94 (m, 2H), 3.54 (br t, J=5.6 Hz, 2H), 2.54–2.45 (m, 2H), 1.42 (s, 9H); TLC [methylene chloride/hexanes, 1:1]: R$_f$=0.2; TLC [diethyl ether]: R$_f$32 0.3.

E. 3-(N-t-Butoxycarbonyl-1,2,5,6-tetrahydropyrid-4-yl)-5-(5-nitropyrid-2-yloxy)-1H-indole 3-(N-t-Butoxycarbonyl-1,2,5,6-tetrahydropyrid-4-yl)-5-hydroxy-1H-indole and 2-chloro-5-nitropyridine were used. Sodium hydride (60% in oil) was the base, tetrahydrofuran was the reaction solvent, the reaction time was heated at reflux (66° C.) for 12 hours, and the chromatographic solvent system was diethyl ether/hexanes [1:3] to afford the title compound (78%) as a yellow foam: $^1$H NMR (CD$_3$OD) δ8.88 (d, J=2.8 Hz, 1H), 8.39 (dd, J=2.8 and 9.1 Hz, 1H), 7.56 (d, J=2.1 Hz, 1H), 7.39 (d, J=8.7 Hz, 1H), 7.31 (s, 1H), 6.94–6.88 (m, 2H), 5.98 (br m, 1H), 4.88 (s, NH), 4.00 (br m, 2H), 3.59 (br t, J=5.3 Hz, 2H), 2.50 (br m, 2H), 1.44 (s, 9H); LRMS (m/z, relative intensity) 436 (M$^+$, 4), 379 (68), 363 (16), 335 (29), 57 (100); TLC [methylene chloride ether, 1:1]: R$_f$=0.5.

EXAMPLE 16

5-Amino-3-(N-t-butoxycarbonylpiperid-4-yl)-1H-indole

A mixture of 3-(N-t-butoxycarbonyl-1,2,5,6-tetrahydropyrid-4-yl)-5-nitro-1H-indole (3.55 g, 10.34 mmol) and 10% palladium on carbon (0.55 g) in absolute ethanol (60 mL) was shaken under a hydrogen atmosphere (3 atm) for 7 hours at room temperature. The resulting reaction mixture was filtered through diatomaceous earth, and the filtrate was evaporated under reduced pressure. The residual solid was triturated in diethyl ether to afford the title compound (2.56 g, 78%) as a pale pink solid: mp, decomposes 215° C.; $^{13}$C NMR (CDCl$_3$) δ155.0, 139.0, 131.3, 127.3, 120.4, 119.8, 112.9, 111.8, 104.1, 79.4, 44.5, 33.8, 32.7, 28.5. Anal. calcd. for C$_{18}$H$_{25}$N$_3$O$_2$·1.4 H$_2$O: C, 67.57; H, 8.03; N, 13.13. Found: C, 67.20; H, 8.07; N, 13.44.

EXAMPLE 17

General Procedure for the Formation of 3-(N-t-Butoxycarbonyl-1,2,5,6-tetrahydropyrid-4-yl)-1H-indoles from Indoles To a stirred solution of sodium (2.51 g, 105 mmol, 7 eq) in absolute methanol (50 mL) was added the indole (15.0 mmol) and N-t-butoxycarbonyl-4-piperidone (8.96 g, 45.0 mmol 3.0 eq). The resulting reaction solution was heated at reflux (65° C.) under nitrogen for 3–24 hours, depending on the indole used. The resulting reaction solution was evaporated under reduced pressure, and the residue was partitioned between a saturated solution of sodium hydrogen carbonate (50 mL) and ethyl acetate (50 mL). The organic layer was removed, and the aqueous layer was extracted with ethyl acetate (2×50 mL). The organic extracts were combined, dried (MgSO$_4$), and evaporated under reduced pressure. The residue was purified either by trituration in diethyl ether or by column chromatography to afford the desired 3-(N-t-butoxycarbonyl-1,2,5,6-tetrahydropyrid-4-yl)-1H-indole.

Following this procedure the following compounds were prepared.

A. 5-Amino-3-(N-t-butoxycarbonyl-1,2,5,6-tetrahydropyrid-4-yl)-1H-indole

5-Aminoindole was used, the reaction reflux was for 5 hours, and the extraction residue was purified via chromatography using silica gel (approximately 200 g) and elution with diethyl ether to afford the title compound (70%) as an off-white foam: $^1$H NMR (CD$_3$OD) δ7.26 (d, J=1.8 Hz, 1H), 7.17 (s, 1H), 7.15 (d, J=8.9 Hz, 1H), 6.70 (dd, J=2.0 and 8.5 Hz, 1H), 6.09–6.03 (m, 1H), 4.88 (s, 3H, exchangeable protons), 4.12–4.06 (m, 2H), 3.63 (br t, J=5.1 Hz, 2H), 2.57–2.47 (m, 2H), 1.49 (s, 9H); TLC [diethyl ether]: R$_f$=0.2.

B. 3-(N-t-Butoxycarbonyl-1,2,5,6-tetrahydropyrid-4-yl)-5-hydroxy-1H-indole

5-Hydroxyindole was used, the reaction reflux was for 3 hours, and the solid extraction residue was triturated in diethyl ether (100 mL) to afford the title compound (88%) as a white solid: mp, decomposes 230° C.; $^{13}$C. NMR (DMSO-$d_6$) δ154.0, 151.1, 131.5, 130.5, 125.2, 123.5, 115.4, 114.8, 112.1, 111.5, 104.2, 78.7, 43.5, 39.2, 38.9, 28.2. Anal. calcd. for $C_{18}H_{22}N_2O_3$: C, 68.77; H, 7.05; N, 8.91. Found: C, 68.73; H, 7.15; N, 8.89.

C. 3-(N-t-Butoxycarbonyl-1,2,5,6-tetrahydropyrid-4-yl)-5-nitro-1H-indole

5-Nitroindole was used, the reaction reflux was 24 hours, and the extraction residue was purified via chromatography using silica gel (approximately 200 g) and elution with ethyl acetate in hexanes [1:2 to 1:1] to afford the title compound (72%) as a yellow solid: mp, decomposes 230° C.; $^1$H NMR (CDCl$_3$) δ9.24 (br s, 1H), 8.78 (d, J=1.3 Hz, 1H), 8.09 (dd, J=1.4 and 9.4 Hz, 1H), 7.40 (d, J=9.3 Hz, 1H), 7.30 (d, J=1.8 Hz, 1H), 6.17–6.15 (m, 1H), 4.16–4.13 (m, 2H), 3.68 (t, J=5.8 Hz, 2H), 2.58–2.48 (m, 2), 1.50 (s, 9H); Anal. calcd. for $C_{15}H_{21}N_3O_4$·0.1 H$_2$O: C, 62.63; H, 6.19; N, 12.17. Found: C, 62.71; N, 6.09; N, 11.81.

EXAMPLE 18

5-Dibenzylamino-1H-indole

To a stirred mixture of 5-aminoindole (3.00 g, 22.7 mmol) and triethylamine (10.5 mL, 74.9 mmol, 3.3 eq) in acetonitrile (30 mL) at room temperature under nitrogen was added benzyl bromide (8.2 mL, 68.9, mmol, 3.0 eq) dropwise. The resulting reaction mixture was heated at reflux under nitrogen for 3 hours. The resulting reaction mixture was filtered, and the filtrate was evaporated under reduced pressure. Column chromatography of the residue using silica gel (approximately 200 g) and elution with ethyl acetate/hexanes [gradient 1:9 to 1:1] afforded the title compound as an off white solid: mp, 124.0°–126.0° C.; $^{13}$C NMR (acetone-$d_6$) δ144.3, 140.8, 131.8, 129.9, 129.2, 128.3, 127.5, 125.7, 113.5, 112.4, 106.4, 101.9, 57.0; TLC [15% ethyl acetate in hexanes]: R$_f$=0.3.

EXAMPLE 19

5-Nitroindole-3-N,N-dimethylglyoxamide

To a stirred mixture of 5-nitroindole (10.00 g, 61.7 mmol) and phthalimide (4.00 g, 40% by weight) in anhydrous ether (250 mL) was added oxalyl chloride (17.0 mL, 0.194 mol, 3.1 eq) dropwise. The resultant reaction mixture was stirred at room temperature under nitrogen for 72 hours. The resulting reaction mixture was chilled in an ice bath (0° C.), and a solution of ether (80 mL) and dimethylamine (80 mL, condensed at −78° C.) was added cautiously with vigorous stirring to the reaction mixture. The resulting mixture was stirred vigorously at room temperature for 1 hour. Ether was then removed from the reaction mixture via evaporation under reduced pressure, and the residue was partitioned between water (500 mL) and methylene chloride (500 mL), The pH of the aqueous layer was adjusted to pH 3 using concentrated HCl, The methylene chloride layer was removed, and the aqueous layer was extracted with methylene chloride (3×500 mL). The methylene chloride extracts were combined, dried (MgSO$_4$), and evaporated under reduced pressure. Recrystallization of the residual solid in refluxing methanol with cooling afforded the title compound (R$_f$=0.15 in 10% acetone in methylene chloride, 5.74 g, 22.0 mmol, 36%) as a pale yellow solid: mp., 248.0°–249.0° C.; IR (KBr) 1755, 1740, 1730, 1650, 1620, 1585, 1530 cm$^{-1}$; $^1$H NMR (DMSO-$d_6$) δ12.9 (br s, NH), 8.97 (d, J=2.3 Hz, 1H), 8.43 (s, 1H), 8.18(dd, J=2.3 and 9.0 Hz, 1H), 7.74 (d, J=9.0 Hz, 1H), 3.02 (s, 3H), 2.95 (s, 3H); $^{13}$C NMR (DMSO-$d_6$) δ166.6, 143.2, 140.4, 140.2, 124.5, 118.9, 117.2, 114.2, 113.6, 36.8, 33.6; LRMS (m/z, relative intensity) 261 (24, M+), 190 (29), 189 (100), 173 (15), 143 (83), 115 (23). HRMS calculated for $C_{12}H_{11}N_3O_4$ 261.0750, found 261.0746. Anal. calcd for $C_{12}H_{11}N_3O_4$: C, 55.17; H, 4.24; N, 16.08. Found: C, 55.15; H, 3.96; N, 15.96.

EXAMPLE 20

3-(2-Dimethylaminoethyl)-5-nitroindole

To a stirred solution of 5-nitroindole-3-N,N-dimethylglyoxamide (5.36 g, 20.52 mmol) in anhydrous tetrahydrofuran (55 mL) was added borane in tetrahydrofuran (1.0M, 78.8 mL, 78.8 mmol, 3.8 eq) dropwise slowly. The resulting reaction solution was stirred at room temperature under nitrogen for 16 hours. A saturated solution of sodium hydrogen carbonate (200 mL) was added carefully to the reaction solution, and the resulting aqueous mixture was extracted with diethyl ether (3×150 mL). The ether extracts were combined, dried (MgSO$_4$), and evaporated under reduced pressure to afford 3-(2-dimethylaminoethyl)-5-nitroindole borane complex as a amorphous orange solid (6.9 g): $^1$H NMR (DMSO-$d_6$) δ11.7 (br m, NH), 8.58 (d, J=2.2 Hz, 1H), 8.00 (dd, J=2.3 and 9.0 Hz, 1H), 7.52 (d, J=8.8 Hz, 1H), 7.49 (br s, 1H), 3.23–3.17 (m, 2H), 3.02–2.97 (m, 2H), 2.63 (s, 6H). This solid was placed in absolute ethanol (150 mL) along with cesium fluoride (6.9 g) and sodium carbonate (6.9 g), and the resulting mixture was heated at reflux under nitrogen for 16 hours. The resulting reaction mixture was filtered through Celite®, and the filtrate was evaporated under reduced pressure. The residual oil was chromatographed using silica gel (approximately 450 g) and elution with methylene chloride/methanol/ammonium hydroxide (8:2:0.1) to afford the title compound (2.58 g, 11.06 mmol, 54%) as a yellow solid: mp, 133.0°–135.0° C.; IR (KBr) 1625, 1575, 1550, 1520, 1480, 1470, 1460, 1445, 1380, 1370, 1330 cm$^{-1}$; $^1$H NMR (DMSO-$d_6$) δ11.55 (br m, NH), 8.48 (d, J=2.2 Hz, 1H), 7.94 (dd, J=2.3 and 9.0 Hz, 1H), 7.47 (d, J=9.0 Hz, 1H), 7.40 (br s, 1H), 2.88–2.83 (m, 2H), 2.53–2.48 (m, 2H), 2.19 (s, 6H); $^{13}$C NMR (DMSO-$d_6$) δ140.2, 139.3, 126.6, 126.5, 116.3, 116.0, 115.6, 111.7, 59.8, 45.1, 22.7; LRMS (m/z, relative intensity) 233 (7, M+), 189 (7), 188 (8), 143 (10), 129 (23), 115 (14), 59 (36), 58 (100). HRMS calculated for $C_{12}H_{15}N_3O_2$ 233.1166, found 233.1155. Anal. calcd for $C_{12}H_{15}N_3O_2$: C, 61.79; H, 6.48; N, 18.01. Found: C, 61.39; H, 6.45; N, 17.68.

EXAMPLE 21

5-Amino-3-(2-dimethylaminoethyl)indole

A mixture of 3-(2-dimethylaminoethyl)-5-nitroindole (1.85 g, 7.93 mmol) and 10% palladium on carbon (0.40 g, 20% by weight) in absolute ethanol (30 mL) was shaken under a hydrogen atmosphere (3 atm) for 6 hours. The resulting mixture was filtered through Celite®, and the celite pad was washed generously with absolute ethanol. The combined filtrates were evaporated under reduced pressure to afford the title compound (1.60 g, 7.87 mmol, 99%) as a clear, slightly dark, hygroscopic oil: IR (CHCl$_3$) 3480, 1610, 1585, 1460, 1335 cm$^{-1}$; $^1$H NMR (CDCl$_3$) δ8.10 (br m, NH), 7.12 (d, J=8.5 Hz, 1H), 6.91 (d, J=2.3 Hz, 1H), 6.88 (d, J=2.2 Hz, 1H), 6.64 (dd, J=2.2 and 8.5 Hz, 1H), 2.89–2.84 (m, 2H), 2.64–2.58 (m, 2H), 2.34 (s, 6H); $^{13}$C NMR (CDCl$_3$) δ139.1, 131.2, 128.3, 122.1, 113.1, 112.9, 111.7, 103.8, 60.3, 45.4, 23.7; LRMS (m/z, relative intensity) 203 (9, M+), 158 (2), 145 (6), 83 (66), 58 (100). HRMS calculated for $C_{12}H_{17}N_3$ 203.1424, found 203.1418. Anal. calcd for $C_{12}H_{17}N_3$·1/2 H$_2$O: C, 67.89; H, 8.55; N, 19.79. Found: C, 67.71; H, 8.60; N, 19.41.

EXAMPLE 22

General Procedure for the Synthesis of N-(Indol-5-yl)-N'-benzoylthioureas

Benzyl chloride (0.68 mL, 5.90 mmol, 1.2 eq) was added portionwise to a stirred solution of ammonium thiocyanate (0.45 g, 5.90 mmol, 1.2 eq) in acetone (10 mL), and the resulting mixture was heated at reflux under nitrogen for 1 hour. To the cooled reaction solution was then added the appropriate 5-aminoindole (5.00 mmol), and this reaction solution was heated at reflux under nitrogen for 3 hours. The resulting reaction mixture was evaporated under reduced pressure, and the residue was placed in a saturated solution of sodium hydrogen carbonate (10 mL). This aqueous mixture was extracted with ethyl acetate (2×10 mL), and the extracts were combined, dried ($Na_2SO_4$), and evaporated under reduced pressure. The residue was column chromatographed using silica gel (approximately 75 g) and elution with 9:1:0.1 [methylene chloride/methanol/ammonium hydroxide] to afford the title compound.

Following this procedure the following compounds were prepared.

A. N-(3-(N-Methylpyrrolidin-2-ylmethyl)-1H-indol-5-yl)-N'-benzoylthiourea (R)-5-Amino-3-(N-methylpyrrolidin-2-ylmethyl)-1H-indole was used. Chromatography afforded the title compound (46%) as a yellow foam: $^{13}$C NMR ($CDCl_3$) δ178.8, 167.0, 135.0, 133.6, 131.7, 129.5, 129.1, 127.6, 127.5, 123.4, 119.2, 115.0, 114.3, 111.4, 66.6, 57.4, 40.8, 31.4, 29.8, 21.8; $[\alpha]^{25}$=+62° [c=2, $CDCl_3$]. Anal. calcd for $C_{22}H_{24}N_4OS.0.4\ CH_2Cl_2$: C, 63.08; H, 5.86; N, 13.14. Found: C, 62.76; H, 5.94; N, 12.94.

B. N-(3-(2-Dimethylaminoethyl)-1H-indol-5-yl)-N'-benzoylthiourea (R)-5-Amino-3-(2-dimethylaminoethyl)-1H-indole was used. Chromatography afforded the title compound (22%) as a yellow foam: $R_f$=0.4 in 9:1:0.1 [methylene chloride/methanol/ammonium hydroxide]; HRMS calculated for $C_{20}H_{22}N_4OS$ 366.1517, found 366.1467. Anal. calcd for $C_{20}H_{22}N_4OS.0.2\ CH_2Cl_2$: C, 63.27; H, 5.89; N, 14.61. Found: C, 63.53; H, 5.83; N, 14.61.

EXAMPLE 23

General Procedure for the Synthesis of N-(indol-5-yl) thioureas

To a stirred solution of the N-(indol-5-yl)-N'-benzoylthiourea (5.5 mol) in absolute ethanol (40 mL) was added dropwise a solution of sodium hydroxide (3.00 g) in water (28 mL). The resulting reaction mixture was heated at reflux for 1 hour. Ethanol was then removed from the reaction mixture via evaporation under reduced pressure, and the pH of the remaining aqueous mixture was brought to pH 10 using concentrated and solid sodium carbonate. This aqueous mixture was extracted with ethyl acetate (3 ×50 mL), and the extracts were combined, dried ($Na_2SO_4$), and evaporated under reduced pressure. The residue was either used as is or crystallized in methylene chloride to afford the title compound.

Following this procedure the following compounds were prepared.

A. N-(3-(N-Methylpyrrolidin-2-ylmethyl)-1H-indol-5-yl) thiourea

The extraction residue directly yielded the title compound (73%) as a yellow solid: $R_f$=0.15 in 10% triethylamine in acetone; $^1$H NMR ($CD_3OD$) δ7.29 (d, J=8.8 Hz, 1H), 7.12 (d, J=2.2 Hz, 1H), 7.11 (s, 1H), 6.78 (dd, J=8.6 and 2.2 Hz, 1H), 4.91 (s, 4H), 3.23–3.13 (m, 2H), 2.75–2.40 (m, 3H), 2.52 (s, 3H), 1.94–1.57 (m, 4H).

B. N-(3-(2-Dimethylaminoethyl)-1H-indol-5-yl)thiourea

Crystallization of the extract residue with methylene chloride afforded the title compound (28%) as a beige solid: mp, 190.0°–191.0° C.; $^{13}$C NMR (acetone-$d_6$) δ183.6, 136.0, 128.9, 124.4, 120.2, 116.4, 115.0, 112.7, 61.1, 45.6, 24.1; HRMS calculated for $[C_{13}H_{18}N_4S.H]^+$263.1333, found 263.1291.

EXAMPLE 24

General Procedure for the Synthesis of 5-(4-Benzyl-1,3-thiaz-2-ylamino)-1H-indoles To a stirred solution of the N-(indol-5-yl)thiourea (1.00 mmol) in absolute ethanol (5 mL) was added 1-phenyl-3-chloro-3-propanone (0.27 g, 1.00 mmol, 1 eq), and the resulting reaction solution was heated at reflux under nitrogen for 3 hours. A saturated solution of sodium hydrogen carbonate (10 mL) was added to the resulting reaction solution and this aqueous mixture was stirred at room temperature for 30 minutes. Ethanol was then removed via evaporation under reduced pressure, and the residual aqueous mixture was extracted with ethyl acetate (2×10 mL). The extracts were combined, dried ($Na_2SO_4$), and evaporated under reduced pressure. The residue was purified either through crystallization or column chromatographed using silica gel (approximately 25 g) and elution with 9:1:0.1 [methylene chloride/methanol/ammonium hydroxide] to afford the title compound.

Following this procedure the following compounds were prepared.

A. 5-(4-Benzyl-1,3-thiaz-2-ylamino)-3-(N-methylpyrrolidin-2-ylmethyl)-1H-indole

Chromatography afforded the title compound (3%) as an off-white solid: $^{13}$C NMR (acetone-$d_6$) δ167.0, 153.1, 140.7, 134.4, 134.0, 129.7, 128.9, 126.7, 124.3, 124.0, 115.5, 113.9, 112.3, 109.4, 101.8, 67.3, 58.0, 41.0, 38.7, 30.5, 22.5; HRMS calculated for $C_{24}H_{26}N_4S$ 402.1881, found 402.1872.

B. 5-(4-Benzyl-1,3-thiaz-2-ylamino)-3-(2-N,N-dimethylaminoethyl)-1H-indole

Trituration of the extraction residue afforded the title compound (20%) as an off-white solid: mp, 170.5°–172.0° C.; $^{13}$C NMR (acetone-$d_6$) δ167.2, 153.1, 140.7, 134.4, 134.1, 129.8, 128.9, 128.8, 126.7, 123.9, 115.7, 114.3, 112.3, 109.4, 101.8, 61.1, 45.6, 38.7, 24.3; HRMS calculated for $C_{22}H_{24}N_4S$ 376.1724, found 376.1724, found 376.1685. Anal. calcd for $C_{22}H_{24}N_4S.0.4\ H_2O$: C, 68.86; H, 6.51; N, 14.60. Found: 68.98; H, 6.18; N, 14.44.

EXAMPLE 25

5-Amino-3-[(2R, 4R)-N-methyl-4-methoxypyrrolidin-2-ylmethyl]-1H-indole

A mixture of 5-(2,5-dimethyl-1H-pyrrolyl)-3-[(2R,4R)-N-methyl-4-methoxypyrrolidin-2-ylmethyl]-1H-indole (2.20 g, 6.52 mmol), hydroxylamine hydrochloride (7.25 g, 104 mmol, 16 eq), and triethylamine (7.28 mL, 52.2 mmol, 8 eq) in 2-propanol (22 mL) was heated at reflux under nitrogen for 8 hours. The resulting reaction solution was evaporated under reduced pressure, and the residue was partitioned between ethyl acetate (50 mL) and a saturated solution of sodium hydrogen carbonate (50 mL). The ethyl acetate layer was removed, and the aqueous layer was extracted with methylene chloride (3×50 mL). All organic extracts were combined, dried (MgSO$_4$), and evaporated under reduced pressure to afford the title compound (1.68 g, 100%) as an off-white amorphous solid: R$_f$=0.4 in 9:1:0.1 [methylene chloride/methanol/ammonium hydroxide]; $^1$H NMR (CD$_3$OD) δ7.14 (d, J=8.5 Hz, 1H), 6.99 (s, 1H), 6.94 (br s, 1H), 6.68 (br d, J=8.5 Hz, 1H), 4.90 (s, 3-NH), 3.86–3.77 (m, 1H), 3.24 (s, 3H), 3.24–3.13 (m, 2H), 2.93–2.80 (m, 1H), 2.69 (dd, J=13.7 and 9.7 Hz, 1H), 2.51 (s, 3H), 2.40–2.18 (m, 2H), 1.73–1.63 (m, 1H); $^{13}$C NMR (CD$_3$OD) δ139.7, 133.4, 129.3, 124.4, 114.4, 112.8, 111.2, 105.5, 79.3, 68.3, 66.1, 56.7, 40.7, 39.5, 30.1.

EXAMPLE 26

5-(2,5-Dimethyl-1H-pyrrolyl)-3-[(2R,4R)-N-methyl-4-methoxypyrrolidin-2-ylmethyl]-1H-indole 3-[(2R,4R)-N-Benzyloxycarbonylpyrrolidin-2-ylcarbonyl)-5-(2,5-dimethyl-1H-pyrrolyl)-1H-indole (3.24 g, 6.87 mmol) was added portionwise as a solid to a mixture of lithium aluminum hydride (1.65 g, 43.5 mmol, 6.3 eq) in anhydrous tetrahydrofuran (80 mL), and the resulting reaction mixture was heated at reflux under nitrogen for 24 hours. To the resulting reaction mixture was added sequentially with care: water (1.65 mL), followed by a solution of sodium hydroxide (2N, 1.65 mL), followed by water (5 mL), followed by ethyl acetate (30 mL). The resulting mixture was stirred at room temperature was 12 hours, and then filtered. The filtrate was evaporated under reduced pressure. The residue was column chromatographed using silica gel (approximately 60 g) and elution with 12:1:0.1 [methylene chloride/methanol/ammonium hydroxide] to afford the title compound (2.20 g, 95%) as a white foam: R$_f$=0.5 in 9:1:0.1 [methylene chloride/methanol/ammonium hydroxide]; $^1$H NMR (CDCl$_3$) δ8.88 (br s, NH), 7.43 (d, J=1.8 Hz, 1H), 7.39 (d, J=8.4 Hz, 1H), 7.11 (d, J=2.2 Hz, 1H), 6.98 (dd, J=8.4 and 1.9 Hz, 1H), 5.94 (s, 2H), 3.80–3.74 (m, 1H), 3.30–3.21 (m, 2H), 3.28 (s, 3H), 2.73 (dd, J=14.1 and 9.6 Hz, 1H), 2.56–2.43 (m, 1H), 2.45 (s, 3H), 2.30 (dd, J=10.9 and 5.6, 1H), 2.25–2.15 (m, 1H), 2.06 (s, 6H), 1.72–1.64 (m, 1H); $^{13}$C NMR (CDCl$_3$) δ135.5, 130.7, 129.4, 128.5, 127.8, 127.0, 123.9, 122.1, 118.4, 113.7, 111.5, 105.0, 78.5, 66.0, 62.5, 56.4, 40.6, 39.2, 29.7, 13.2; FAB HRMS calculated for [C$_{21}$H$_{27}$N$_3$O H] 338.2234, found 338.2247.

EXAMPLE 27

3-[(2R,4R)-N-Benzyloxycarbonylrrolidin-2-ylcarbonyl)-5-(2,5-dimethyl-1H-pyrrolyl)-1H-indole To a stirred solution of (2R,4R)-4-methoxyproline [Krapcho, et. al, *J. Med. Chem*, 1148 (1988)] (5.22 g, 18.8 mmol) in anhydrous methylene chloride (50 mL) with a trace of N,N-dimethylformamide (0.5 mL) was added dropwise oxalyl chloride (2.44 mL, 28.0 mmol, 1.5 eq). The resulting effervescing solution was stirred at room temperature under nitrogen for 2 hours. The reaction solution was then evaporated under reduced pressure, chased with hexanes (2×20 mL), and the residue proline acid chloride was dissolved in benzene (25 mL). Concomitantly, to a stirred solution of 5-(2,5-dimethyl-1H-pyrrolyl)-1H-indole (7.22 g, 38.0 mmol, 2.0 eq) in benzene (30 mL) was added a solution of ethyl magnesium bromide (3.0M in ether, 13.0 mL, 39 mmol, 2.0 eq), and the resulting effervescing solution was stirred at room temperature under nitrogen for 30 minutes, and then it was cooled to 0° C. To this cooled (0° C.) solution of the indole magnesium salt was added the benzene solution of the proline acid chloride rapidly with vigorous stirring. The resulting reaction mixture was stirred at 0° C. under nitrogen for 10 minutes. A saturated solution of sodium hydrogen carbonate (80 mL) was then added, and this aqueous mixture was extracted with ethyl acetate (2×80 mL). The organic extracts were combined, dried (MgSO$_4$), and evaporated under reduced pressure. The residual oil was crystallized by stirring in diethyl ether (80 mL) overnight to afford the title compound (7.15 g, 81%) as a white solid: mp 189.0°–191.0° C.; R$_f$=0.4 in ethyl acetate/hexanes [2:1]; FAB HRMS calculated for [C$_{28}$H$_{29}$N$_3$O$_4$H] 472.2238, found 472.2281.

EXAMPLE 28

5-(2,5-Dimethyl-1H-pyrrolyl)-1H-indole

A mixture of 5-aminoindole (1.32 g, 10.0 mmol), acetonylacetone (4.0 mL, 34 mmol, 3.4 eq) and toluene (25 mL) was heated at reflux under nitrogen using a Dean-Stark trap for 24 hours. The reaction was cooled and then poured through a silica gel (approximately 200 g) filter followed by 10% ether in hexanes to afford the title compound (1.52 g, 72%) as an off-white, crystalline solid: R$_f$=0.75 in diethyl ether; $^{13}$C NMR (CDCl$_3$) δ135.0, 131.4, 129.5, 128.1, 125.6, 122.4, 120.3, 111.3, 105.0, 103.0, 13.2. Anal. calcd for C$_{14}$H$_{14}$N$_2$; C, 79.97; H, 6.71; N, 13.32. Found: C, 79.72; H, 6.75; N, 13.13.

I claim:

1. A compound of the formula

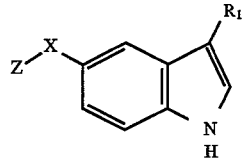

wherein Z is

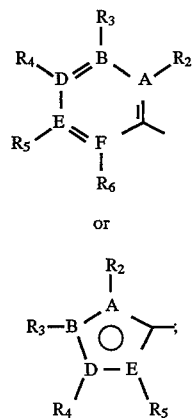

or

R$_1$ is

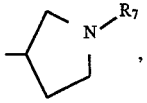

-continued

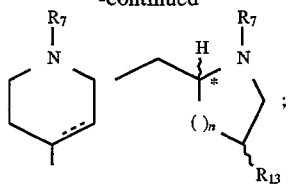

X is O, NH, or S; A, B, D, E, and F are each independently C, N, O, or S; $R_2$, $R_3$, $R_4$, $R_5$, and $R_6$ are each independently hydrogen, $C_1$ to $C_6$ alkyl, aryl, $C_1$ to $C_3$ alkyl-aryl, halogen, cyano, nitro, —$NR_7R_8$, —$(CH_2)_mOR_9$, —$SR_9$, —$SO_2R_9$, —$SO_2NR_7R_8$, —$NR_7SO_2R_8$, —$NR_7CO_2R_9$, —$NR_7COR_9$, —$CONR_7R_8$ or —$CO_2R_9$; one of $R_2$ and $R_3$, $R_3$ and $R_4$, $R_4$ and $R_5$, or $R_5$ and $R_6$ may be taken together to form a five- to seven-membered alkyl ring, a six- membered aryl ring, a five- to seven-membered heteroalkyl ring having 1 heteroatom of N, O, or S, or a five-or six-membered heteroaryl ring having 1 or 2 heteroatoms of N, O, or S; $R_7$ and $R_8$ are each independently hydrogen, $C_1$ to $C_7$ alkyl, —$(CH_2)_qR_{10}$, $C_1$ to $C_3$ alkyl-aryl, aryl, or $R_7$ and $R_8$ may be taken together to form a four- to six-membered ring; $R_9$ is hydrogen, $C_1$ to $C_6$ alkyl, $C_1$ to $C_3$ alkyl-aryl, aryl, or —$(CH_2)_wR_{11}$; $R_{10}$ and $R_{11}$ are each independently —OH, —$OR_{12}$, —$CO_2R_{12}$, —$CONHR_{12}$, or cyano; $R_{12}$ is hydrogen, $C_1$ to $C_6$ alkyl, aryl, or $C_1$ to $C_6$ alkyl-aryl; $R_{13}$ is hydrogen, —$OR_{14}$, or —$NHCOR_{14}$; $R_{14}$ is $C_1$ to $C_6$ alkyl or $C_1$ to $C_3$ alkyl-aryl; n is 0, 1, or 2; m is 1, 2, or 3; q is 2, 3, or 4; w is 2, 3, or 4; the above aryl groups and the aryl moieties of the above alkyl-aryl groups are independently phenyl or substituted phenyl, wherein said substituted phenyl may be substituted with one to three of $C_1$ to $C_4$ alkyl, halogen, hydroxy, cyano, carboxamido, nitro, and $C_1$ to $C_4$ alkoxy; and a broken line represents an optional double bond, with the proviso that when Z is phenyl where $R_2$, $R_3$, $R_4$, $R_5$, and $R_6$ are each hydrogen and $R_1$ is

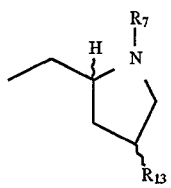

then X is S or NH, and the pharmaceutically acceptable salts thereof.

2. A compound according to claim 1, wherein $R_1$ is

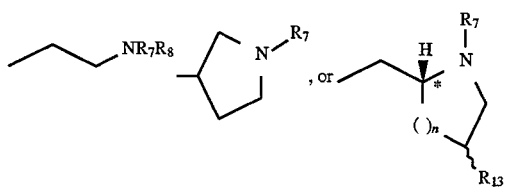

where $R_7$, $R_8$ and $R_{13}$ are as defined in claim 1.

3. A compound according to claim 2 wherein Z is

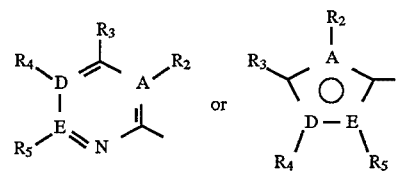

where A, D, E, $R_2$, $R_3$, $R_4$, and $R_5$ are as defined in claim 1; and X is NH.

4. A compound according to claim 3 where in $R_1$ is

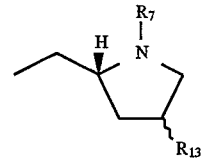

where $R_7$ and $R_{13}$ is defined in claim 1.

5. A compound according to claim 4, wherein $R_{13}$ is hydrogen.

6. A compound according to claim 4, wherein Z is

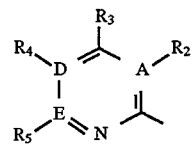

where A, D, E, $R_2$, $R_3$, $R_4$, and $R_5$ are as defined in claim 1; and X is NH.

7. A compound according to claim 2 wherein $R_1$ is

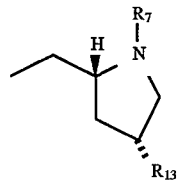

where $R_7$ and $R_{13}$ are as defined in claim 1.

8. A compound according to claim 7, wherein $R_{13}$ is —$OR_{14}$ and $R_{14}$ is —$CH_3$.

9. A compound according to claim 7 wherein Z is

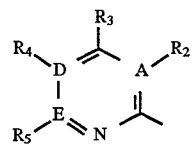

where A, D, E, $R_2$, $R_3$, $R_4$, and $R_5$ are as defined in claim 1; and X is NH.

10. A compound according to claim 3 wherein Z is

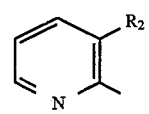

wherein $R_2$ is $NO_2$, CN, $SO_2CH_3$, $SO_2Ph$, $CONH_2$ and X is NH.

11. A compound according to claim 10 wherein $R_1$ is

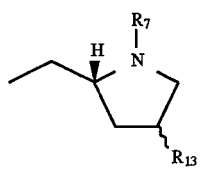

wherein $R_7$ and $R_{13}$ are as defined in claim 1.

12. A compound according to claim 1, said compound being selected from 3-(2-dimethylaminoethyl)-5-(3,5-dinitropyrid-2-ylamino)-1H-indole;

3-(2-dimethylaminoethyl)-5-(3-nitropyrid-2-ylamino)-1H-indole;

3-(2-dimethylaminoethyl)-5-(3-trifluoromethylpyrid-2-ylamino)-1H-indole;

(R)-5-(3-nitropyrid-2-ylamino)-3-(pyrrolidin-2-ylmethyl)-1H-indole;

(R)-3-(N-methylpyrrolidin-2-ylmethyl)-5-(nitropyrid-2-ylamino)-1H-indole; 1

(R,S)-3-(N-methylpyrrolidin-3-yl)-5-(3-nitropyrid-2-ylamino)-1H-indole;

5-(benzoxaz-2-ylamino)-3-(2-dimethylaminoethyl)-1H-indole;

(R)-3-(N-cyclopropylmethylpyrrolidin-2-ylmethyl)-5-(3-nitropyrid-2-ylamino)-1H-indole;

(R)-5-(3-nitropyrid-2-ylamino)-3-(N-(2-propenyl) pyrrolidin-2-ylmethyl)-1H-indole;

(R)-5-(3-nitropyrid-2-ylamino)-3-(N-(2-propenyl) pyrrolidin-2-ylmethyl)-1H-indole;

(R)-5-(3-nitropyrid-2-ylamino)-3-(N-propylpyrrolidin-2-ylmethyl)-1H-indole;

(R)-3-(N-butylpyrrolidin-2-ylmethyl)-5-(3-nitropyrid-2-ylamino)-1H-indole;

(R)-3-(N-ethylpyrrolidin-2-ylmethyl)-5-(3-nitropyrid-2-ylamino)-1H-indole;

(R)-5-(3-nitropyrid-2-ylamino)-3-(N-pentylpyrrolidin-2-ylmethyl)-1H-indole;

(R)-3-(N-(2-methoxyethyl)pyrrolidin-2-ylmethyl)-5-(3-nitropyrid-2-ylamino)-1H-indole;

(R)-3-(N-(2-cyanoethyl)pyrrolidin-2-ylmethyl)-5-(3-nitropyrid-2-ylamino)-1H-indole;

(R)-3-(N-(2-cyanomethyl)pyrrolidin-2-ylmethyl)-5-(3-nitropyrid-2-yl-amino)-1H-indole;

5-(4-benzyl-1,3-thiaz-2-ylamino)-3-(2-dimethylaminoethyl)-1H-indole;

(R)-5-(3-benzylthio-1,2,4-thiadiaz-5-ylamino)-3-(N-methylpyrrolidin-2-ylmethyl)-1H-indole;

3-(2-dimethylaminoethyl)-5-(pyrimid-2-ylamino)-1H-indole;

3-(2-dimethylaminoethyl)-5-(3-methylsulfonylpyrid-2-ylamino)-1H-indole;

(R)-3-(N-methylpyrrolidin-2-ylmethyl)-5-(2-nitrophenylamino)-1H-indole;

(R)-5-(6-methoxy-3-nitropyrid-2-ylamino)-3-(N-methylpyrrolidin-2-ylmethyl)-1H-indole;

(R)-5-(4-methyl-3-nitropyrid-2-ylamino)-3-(N-methylpyrrolidin-2-ylmethyl)-1H-indole;

(R)-3-(N-methylpyrrolidin-2-ylmethyl)-5-(3-nitro-5-phenylpyrid-2-ylamino)-1H-indole;

(R)-5-(3-cyanopyrid-2-ylamino)-3-(N-methylpyrrolidin-2-ylmethyl)-1H-indole;

(R)-5-(6-isopropoxy-3-nitropyrid-2-ylamino)-3-(N-methylpyrrolidin-2-ylmethyl)-1H-indole;

(R)-5-(4-cyano-2-nitrophenylamino)-3-(N-methylpyrrolidin-2-ylmethyl)-1H-indole;

(R)-3-(N-methylpyrrolidin-2-ylmethyl)-5-(4-trifluoromethyl-2-nitrophenylamino)-1H-indole;

(R)-5-(5,6-dichloro-2-nitrophenylamino)-3-(N-methylpyrrolidin-2-ylmethyl)-1H-indole;

5-(4-Cyano-2-nitrophenylamino)-3-[(2R,4R)-N-methyl-4-methoxypyrrolidin-2-ylmethyl]-1H-indole;

5-(4-benzyl-1,3-thiaz-2-ylamino)-3-(2-dimethylaminoethyl)-1H-indole;

(R)-5-(3-benzylthio-1,2,4-thiadiaz-5-ylamino)-3-(N-methylpyrrolidin-2-ylmethyl)-1H-indole; and (R)-5-(5-chloro-2-nitrophenylamino)-3-(N-methylpyrrolidin-2-ylmethyl)-1H-indole.

13. A pharmaceutical composition for treating a condition selected from hypertension, depression, anxiety, eating disorders, obesity, drug abuse, cluster headache, migraine, pain, and chronic paroxysmal hemicrania and headache associated with vascular disorders comprising an amount of a compound according to claim 1 effective in treating such condition and a pharmaceutically acceptable carrier.

14. A pharmaceutical composition for treating disorders arising from deficient serotonergic neurotransmission comprising an amount of a compound according to claim 1 effective in treating such a disorder and a pharmaceutically acceptable carrier.

15. A method for treating a condition selected from hypertension, depression, anxiety, eating disorders, obesity, drug abuse, cluster headache, migraine, pain and chronic paroxysmal hemicrania and headache associated with vascular disorders comprising administering to e mammal requiring such treatment an amount of a compound according to claim 1 effective in treating such condition.

16. A method for treating disorders arising from deficient serotonergic neurotransmission comprising administering to a mammal requiting such treatment an amount of a compound according to claim 1 effective in treating such condition.

* * * * *